United States Patent
Jin

(10) Patent No.: US 12,064,468 B2
(45) Date of Patent: Aug. 20, 2024

(54) **COMPOSITIONS AND METHODS RELATING TO A C-TERMINAL PEPTIDE OF TROPONIN I WITH ACTIVITY AS A MYOFILAMENT CA

COMPOSITIONS AND METHODS RELATING TO A C-TERMINAL PEPTIDE OF TROPONIN I WITH ACTIVITY AS A MYOFILAMENT CA2+ DESENSITIZER

REFERENCE TO RELATED APPLICATION

This application claims priority to U.S. Provisional Patent Application Ser. No. 62/883,958, filed Aug. 7, 2019, the entire content of which is incorporated herein by reference.

GRANT REFERENCE

This invention was made with government support under Grant Nos. HL-127691 and 138007, awarded by the National Institutes of Health. The Government has certain rights in the invention.

BACKGROUND OF THE INVENTION

Heart failure is the most common end stage condition of cardiovascular diseases. Diastolic heart failure, i.e., heart failure with preserved ejection fraction, HFpEF, is a challenging clinical condition characterized by the inefficient filling of the heart chambers during diastole resulting in reduced stroke volume based on the Frank-Starling mechanism, see V. Melenovsky et al., Journal of the American College of Cardiology 49(2) (2007) 198-207; H. A. Shiels et al., Journal of Experimental Biology 211(13) (2008) 2005-2013; and D. G. Allen et al., Journal of Molecular and Cellular Cardiology 17(9) (1985) 821-840.

Muscle contraction is vital in animal mobility and heart function. Skeletal and cardiac muscles are striated muscles in which contraction is generated by the interaction of sarcomeric thick and thin filaments in the crossbridge ATPase cycle. The thick filaments are mainly composed of the motor protein myosin, while the thin filaments are composed of actin and the regulatory proteins tropomyosin and troponin. The troponin complex contains three protein subunits: the calcium-binding subunit (troponin C, TnC), the inhibitory subunit (troponin I, TnI), and the tropomyosin-binding subunit (troponin T, TnT). The contraction of myocytes is initiated by the rise of cytosolic $Ca^{2+}$ that binds TnC and induces a series of allosteric changes in troponin and the thin filament to allow myosin heads to bind actin, which activates myosin ATPase and crossbridge cycling to generate power strokes. Subsequent decline of cytosolic $Ca^{2+}$ results in dissociation of $Ca^{2+}$ from troponin to return the thin filament to the inhibitory state, detachment of myosin heads from the thin filament, and relaxation of the myocyte.

The primary function of troponin as a $Ca^{2+}$-regulated brake in the sarcomere involves the key function of TnI that is responsible for the inhibition of myosin ATPase and muscle relaxation. Encoded by homologous genes, three muscle fiber type-specific isoforms of TnI have evolved in vertebrates. With the exception that cardiac TnI has a unique N-terminal extension, the structures of cardiac, fast and slow skeletal muscle TnI isoforms are highly conserved, see for example, J.-P. Jin et al., Biochemistry 40(8) (2001) 2623-2631; and J.-J. Sheng et al., Gene 576(1) (2016) 385-394. The C-terminal end segment of TnI encoded by the last exon is one of the most conserved structures in the three isoforms and across vertebrate species, see J.-J. Sheng et al., Gene 576(1) (2016) 385-394 and FIG. 1.

Mutations in the C-terminal end segment of cardiac TnI are associated with cardiomyopathies, the majority of which present clinically with diastolic dysfunction (i.e., hypertrophic cardiomyopathy, HCM; and restrictive cardiomyopathy, RCM), see for example, F. I. Gambarin et al., Heart 94(10) (2008) 1257; A. Doolan et al., Journal of Molecular and Cellular Cardiology 38(2) (2005) 387-393; Q.-W. Lu et al., Morimoto, Journal of geriatric cardiology 10(1) (2013) 91-101; M. S. Parvatiyar et al., Journal of Biomedicine and Biotechnology 2010 (2010) 1-9; R. H. Willott et al., Journal of Molecular and Cellular Cardiology 48(5) (2010) 882-892; and J.-J. Sheng et al., Frontiers in Physiology 5 (2014) 165. An extensively studied RCM mutation, R192H, (see FIG. 1) has been shown to cause severe diastolic dysfunction of the heart, as described in J. Du et al., Archives of Biochemistry and Biophysics 456(2) (2006) 143-150. The hearts of transgenic mice expressing C-terminal 19 amino acid-deleted cardiac TnI also demonstrated severely impaired diastolic function as described in A. M. Murphy et al., Science 287(5452) (2000) 488-491. This site is a $Ca^{2+}$-regulated structural and functional domain of the troponin complex with a saturable binding to tropomyosin in low $Ca^{2+}$ state, as described in Z. Zhang et al., The FEBS Journal 278(18) (2011) 3348-3359, indicating a role in the inhibitory activity of TnI during muscle relaxation. This segment has also been implicated as a mobile domain that is able to dock to the actin thin filament in a $Ca^{2+}$-dependent manner, see K. Murakami et al., Journal of Molecular Biology 352(1) (2005) 178-201.

The C-terminal end segment of TnI was not resolved in the static crystallographic structures of troponin complexes of both cardiac muscle, see S. Takeda et al., Nature 424 (6944) (2003) 35, and skeletal muscle, see M. V. Vinogradova et al., Proceedings of the National Academy of Sciences 102(14) (2005) 5038-5043, potentially due to its allosteric nature. On the other hand, the C-terminal end segment of TnI forms a conserved epitope structure that is recognized by a monoclonal antibody (mAb) TnI-1, see FIG. 1 and see S. Akhter et al., FEBS Open Bio 5 (2015) 64-75. Consistent with its binding to tropomyosin when residing in troponin complex, this epitope is an exposed structure for affinity chromatographic isolation, see Z. Zhang et al., Biochemistry 45(38) (2007) 11681-11694, or immunoprecipitation of the entire troponin complex, see Z.-B. Yu et al., Journal of Biological Chemistry 276(19) (2001) 15753-15760. Further supporting the functional importance of the folded structure of the C-terminal end segment of TnI, the single amino acid substitution RCM mutation R192H abolishes the epitope recognized by mAb TnI-1, see Y. Li et al., Journal of Molecular and Cellular Cardiology 62 (2013) 227-236.

After decades of intensive research and numerous clinical trials, specific and effective treatments for heart failure remain to be developed, see C. Satpathy et al., American Family Physician 73(5) (2006) 841-846; and J.-W. Ha et al., Journal of Cardiovascular Ultrasound 17(3) (2009) 86-95. Pharmacological therapy for diastolic dysfunction is currently multifactorial and involves addressing diuresis, heart rate control, reducing myocardial hypertrophy and ventricular relaxation, see C. Satpathy et al., American Family Physician 73(5) (2006) 841-846; J.-W. Ha et al., Journal of Cardiovascular Ultrasound 17(3) (2009) 86-95; and F. Aziz et al., Journal of Clinical Medicine Research 5(5) (2013) 327-334. Beta blockers have been commonly utilized in the treatment of heart failure by enhancing ventricular filling and lowering vascular resistance; however, beta blockers are notably negative inotropes and thereby have the potential to weaken force production, see P. Arlock, B. et al., Scandinavian Cardiovascular Journal 39(4) (2005) 250-254; and M. R. Bristow et al., Journal of Cardiac Failure 7(2) (2001)

8-12. On the other hand, positively inotropic drug such as digitalis and other $Ca^{2+}$ enhancers drastically increase myocardial energetic expenditure with very limited long-term benefit, see S. Sasayama, Cardiovascular Drugs and Therapy, 10(6) (1997) 703-709.

There is a continuing need for compositions and methods for treatment that reduces muscle sensitivity to $Ca^{2+}$ without decreasing maximum force production to ameliorate conditions such as disorders of skeletal muscle and/or cardiac muscle, particularly heart failure. There is a continuing need for compositions and methods targeting specific steps of the cardiac muscle contraction and relaxation cycle to treat heart failure, particularly diastolic heart failure.

SUMMARY OF THE INVENTION

Methods of treating a disorder of cardiac muscle and/or skeletal muscle in a subject according to aspects of the present disclosure which include administering a therapeutically effective dose of a C-terminal portion of troponin I capable of reduction of cardiac muscle and/or skeletal muscle sensitivity to $Ca^{2+}$ without decreasing maximum force production. According to aspects of the present disclosure, the subject is a human being.

Methods of treating a disorder of cardiac muscle and/or skeletal muscle in a subject according to aspects of the present disclosure which include administering a therapeutically effective dose of a C-terminal portion of troponin I capable of reduction of cardiac muscle and/or skeletal muscle sensitivity to $Ca^{2+}$ without decreasing maximum force production, wherein the C-terminal portion of troponin I is or includes a peptide selected from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:32, and a variant of any thereof.

Methods of treating a disorder of cardiac muscle and/or skeletal muscle in a subject according to aspects of the present disclosure which include administering a therapeutically effective dose of a C-terminal portion of troponin I capable of reduction of cardiac muscle and/or skeletal muscle sensitivity to $Ca^{2+}$ without decreasing maximum force production, wherein the C-terminal portion of troponin I is or includes a variant of a peptide selected from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:32, wherein the variant includes one or more conservative amino acid substitutions compared to the peptide selected from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:32, and wherein the variant is capable of reduction of cardiac muscle and/or skeletal muscle sensitivity to $Ca^{2+}$ without decreasing maximum force production.

Methods of treating a disorder of cardiac muscle and/or skeletal muscle in a subject according to aspects of the present disclosure which include administering a therapeutically effective dose of a C-terminal portion of troponin I capable of reduction of cardiac muscle and/or skeletal muscle sensitivity to $Ca^{2+}$ without decreasing maximum force production, wherein the C-terminal portion of troponin I is or includes a variant of a peptide selected from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:32, wherein the variant has at least 70% identity, at least 80% identity, at least 90% identity, or at least 95% identity to the peptide selected from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:32, and wherein the variant is capable of reduction of cardiac muscle and/or skeletal muscle sensitivity to $Ca^{2+}$ without decreasing maximum force production.

Methods of treating a disorder of cardiac muscle and/or skeletal muscle in a subject according to aspects of the present disclosure which include administering a therapeutically effective dose of a C-terminal portion of troponin I capable of reduction of cardiac muscle and/or skeletal muscle sensitivity to $Ca^{2+}$ without decreasing maximum force production, wherein the C-terminal portion of troponin I is or includes a variant of a peptide of SEQ ID NO:32, wherein the variant has at least 22 amino acids, wherein the variant includes one or more conservative amino acid substitutions compared to SEQ ID NO:32, wherein the variant has at least 70% identity, at least 80% identity, at least 90% identity, or at least 95% identity to SEQ ID NO:32, and wherein the variant is capable of reduction of cardiac muscle and/or skeletal muscle sensitivity to $Ca^{2+}$ without decreasing maximum force production.

Methods of treating a disorder of cardiac muscle and/or skeletal muscle in a subject according to aspects of the present disclosure which include administering a therapeutically effective dose of a C-terminal portion of troponin I capable of reduction of cardiac muscle and/or skeletal muscle sensitivity to $Ca^{2+}$ without decreasing maximum force production, wherein the C-terminal portion of troponin I is or includes a variant of a peptide of SEQ ID NO:1, wherein the variant has at least 23 amino acids, wherein the variant comprises one or more conservative amino acid substitutions compared to SEQ ID NO:1, wherein the variant has at least 70% identity, at least 80% identity, at least 90% identity, or at least 95% identity to SEQ ID NO:1, and wherein the variant is capable of reduction of cardiac muscle and/or skeletal muscle sensitivity to $Ca^{2+}$ without decreasing maximum force production.

Methods of treating a disorder of cardiac muscle and/or skeletal muscle in a subject according to aspects of the present disclosure which include administering a therapeutically effective dose of a C-terminal portion of troponin I capable of reduction of cardiac muscle and/or skeletal muscle sensitivity to $Ca^{2+}$ without decreasing maximum force production, wherein the C-terminal portion of troponin I is or includes a variant of a peptide of SEQ ID NO:3, wherein the variant has at least 27 amino acids, wherein the variant comprises one or more conservative amino acid substitutions compared to SEQ ID NO:3, wherein the variant has at least 70% identity, at least 80% identity, at least 90% identity, or at least 95% identity to SEQ ID NO:3, and wherein the variant is capable of reduction of cardiac muscle and/or skeletal muscle sensitivity to $Ca^{2+}$ without decreasing maximum force production.

According to aspects of the present disclosure, one or more additional therapeutic agents is administered to the subject to treat a disorder of cardiac muscle and/or skeletal muscle in the subject.

According to aspects of the present disclosure, administering a therapeutically effective dose of a C-terminal portion of troponin I, includes administering an expression cassette, wherein the expression cassette includes a nucleic acid encoding the C-terminal portion of troponin I, operably linked to a promoter. According to aspects of the present disclosure, the promoter is capable of driving expression of the nucleic acid encoding the C-terminal portion of troponin I in cardiac muscle and/or skeletal muscle. According to aspects of the present disclosure, the promoter is a cardiac muscle protein promoter or a skeletal muscle protein promoter. According to further aspects of the present disclosure, the promoter is selected from the group consisting of: human cardiac troponin I (hcTnI) promoter, human cardiac troponin T (hcTnT) promoter, human cardiac myosin-binding protein C promoter, human cardiac myosin light chain 2V promoter, human alpha cardiac myosin heavy chain promoter, and human beta cardiac myosin heavy chain promoter.

According to aspects of methods of treating a disorder of cardiac muscle in a subject according to aspects of the present disclosure, the subject has heart failure.

According to aspects of methods of treating a disorder of cardiac muscle in a subject according to aspects of the present disclosure, the subject has a cardiac disorder relating to mutation of troponin or other sarcomeric proteins, such as hypertrophic cardiomyopathy (HCM), restrictive cardiomyopathy (RCM), and dilated cardiomyopathy (DCM).

According to aspects of methods of treating a disorder of skeletal muscle in a subject according to aspects of the present disclosure, the subject has a coordination disorder of the skeletal muscles.

Pharmaceutical compositions are provided according to aspects of the present disclosure which include a C-terminal portion of troponin I capable of reduction of cardiac muscle and/or skeletal muscle sensitivity to $Ca^{2+}$ without decreasing maximum force production.

Pharmaceutical compositions are provided according to aspects of the present disclosure which include a nucleic acid encoding the C-terminal portion of troponin I capable of reduction of cardiac muscle and/or skeletal muscle sensitivity to $Ca^{2+}$ without decreasing maximum force production.

Pharmaceutical compositions are provided according to aspects of the present disclosure which include a nucleic acid encoding the C-terminal portion of troponin I capable of reduction of cardiac muscle and/or skeletal muscle sensitivity to $Ca^{2+}$ without decreasing maximum force production, wherein the nucleic acid is included in an expression cassette and is operably linked to a promoter.

Pharmaceutical compositions are provided according to aspects of the present disclosure which include a nucleic acid encoding the C-terminal portion of troponin I capable of reduction of cardiac muscle and/or skeletal muscle sensitivity to $Ca^{2+}$ without decreasing maximum force production, wherein the nucleic acid is included in an expression cassette and is operably linked to a promoter, wherein the promoter is capable of driving expression of the nucleic acid encoding the C-terminal portion of troponin I in cardiac muscle and/or skeletal muscle.

Pharmaceutical compositions are provided according to aspects of the present disclosure which include a nucleic acid encoding the C-terminal portion of troponin I capable of reduction of cardiac muscle and/or skeletal muscle sensitivity to $Ca^{2+}$ without decreasing maximum force production, wherein the nucleic acid is included in an expression cassette and is operably linked to a promoter, wherein the promoter is capable of driving expression of the nucleic acid encoding the C-terminal portion of troponin I in cardiac muscle and/or skeletal muscle, and wherein the expression cassette is included in a vector.

Assays for identification of a test compound capable of reduction of cardiac muscle and/or skeletal muscle sensitivity to $Ca^{2+}$ without decreasing maximum force production are provided according to aspects of the present disclosure which include contacting human alpha-tropomyosin, or a non-human homologue thereof, with a test compound under conditions that promote specific interaction between the tropomyosin and the test compound, and detecting a change in reduction of cardiac muscle and/or skeletal muscle sensitivity to $Ca^{2+}$ without decreasing maximum force production, if present.

DETAILED DESCRIPTION OF THE INVENTION

Figure 1A:
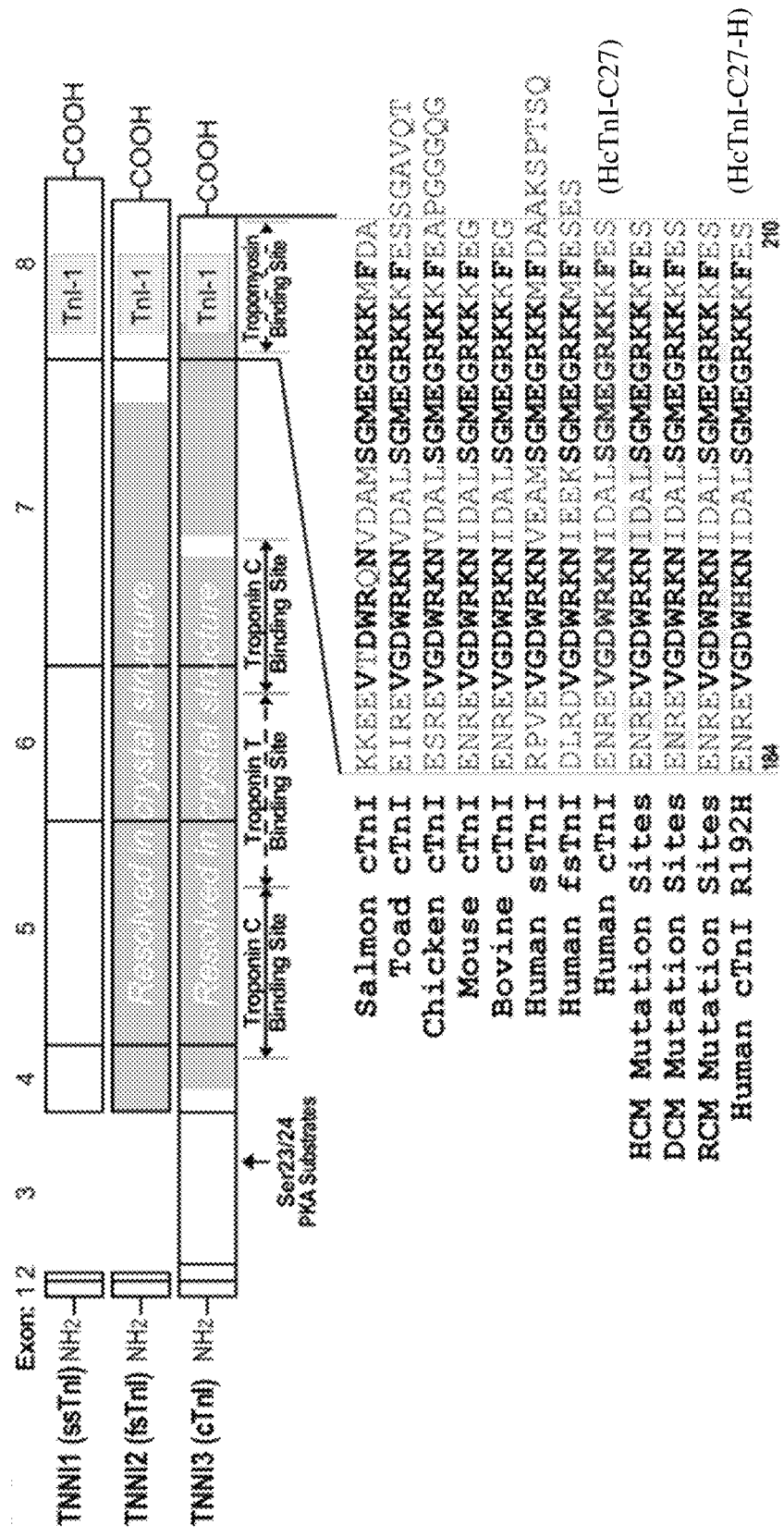
FIG. 1A is a diagram showing the highly conserved C-terminal end segment of TnI. Linear structures of the three isoforms of human TnI are shown schematically with their exon organizations, major functional sites and the location of mAb TnI-1 epitope. The regions resolved in the crystal structure of human cardiac troponin and chicken fast skeletal muscle troponin are shaded. The highly conserved amino acid sequence alignment of the exon 8-encoded C-terminal end segment of cardiac (cTnI), slow skeletal muscle (ssTnI) and fast skeletal muscle (fsTnI) isoforms of TnI from representative vertebrate species demonstrates the conserved core structure. The most conserved residues are bolded. The known mutation sites that cause hypertrophic cardiomyopathies (HCM), dilated cardiomyopathies (DCM) and restrictive cardiomyopathies (RCM) are highlighted in gray indicate changes in the conserved region would cause impaired cardiac function (although they do not completely abolish troponin function as non-lethal mutations including the most severe mutation R192H shown in the bottom). Sequences shown in FIG. 1A include: Salmon cTnI—SEQ ID NO:4; Toad cTnI—SEQ ID NO:6; Chicken cTnI—SEQ ID NO:8; Mouse cTnI—SEQ ID NO:9; Bovine cTnI—SEQ ID NO:9; Human ssTnI—SEQ ID NO:10; Human fsTnI—SEQ ID NO:11; Human cTnI—aka HcTnT-C27—SEQ ID NO:3; Human Mutation Sites in SEQ ID NO:3 with highlighting to show HCM mutations; DCM Mutation Sites in SEQ ID NO:3 with highlighting to show DCM mutations; RCM Mutation Sites in SEQ ID NO:3 with highlighting to show RCM mutations; and Human cTnI—R192H, also called HcTnT-C27-H herein, in SEQ ID NO:3.
Figure 1B:
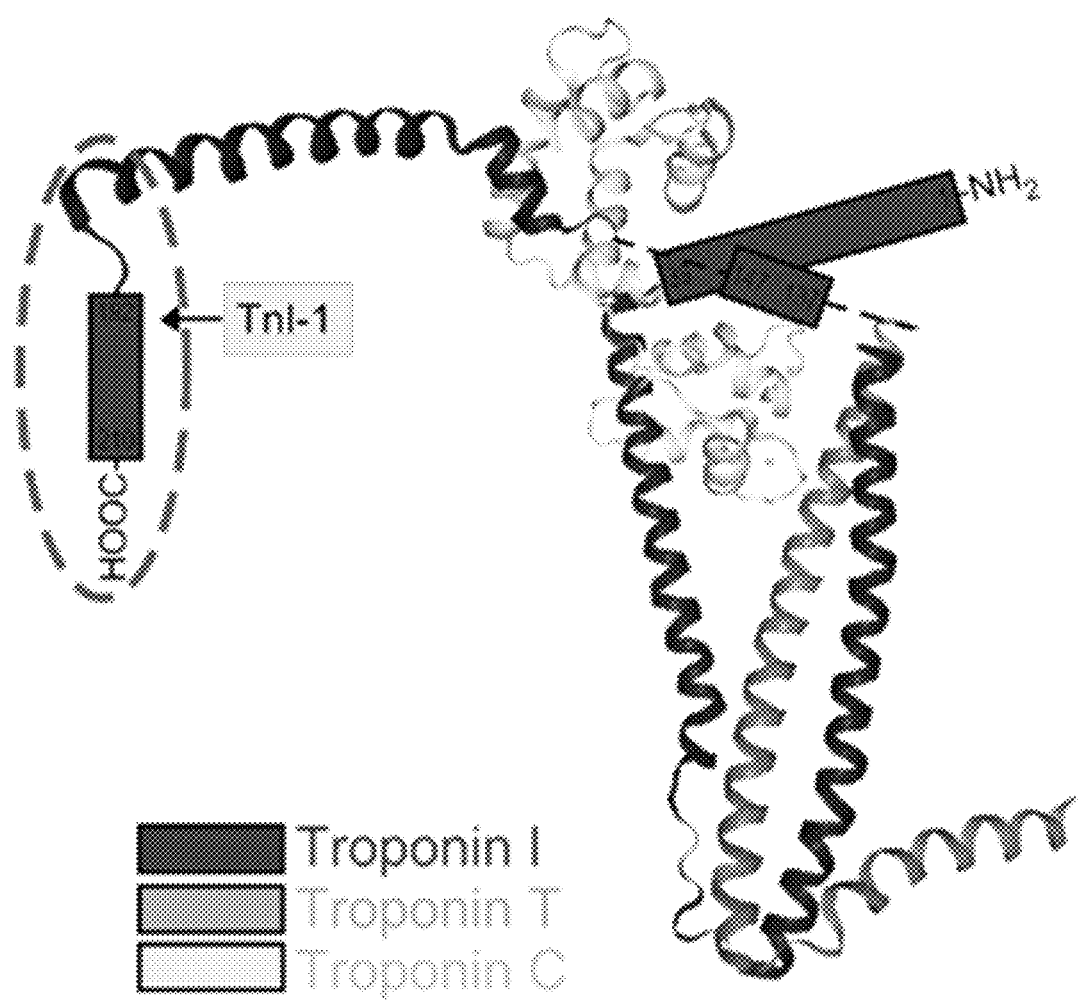
FIG. 1B is a diagram showing the crystal structure of cardiac troponin complex is depicted (PDB ID: 1J1E) to illustrate the position of TnI C-terminal end segment (in the dashed oval) among the unresolved regions.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W. H. Freeman & Company, 2004; Herdewijn, P. (Ed.), Oligonucleotide Synthesis: Methods and Applications, Methods in Molecular Biology, Humana Press, 2004; Remington: The Science and Practice of Pharmacy, Lippincott Williams & Wilkins, 21st Ed., 2005; L. V. Allen, Jr. et al., Ansel's Pharmaceutical Dosage Forms and Drug Delivery Systems, 8th Ed., Philadelphia, PA: Lippincott, Williams & Wilkins, 2004; and L. Brunton et al., Goodman & Gilman's The Pharmacological Basis of Therapeutics, McGraw-Hill Professional, 12th Ed., 2011.

The singular terms "a," "an," and "the" are not intended to be limiting and include plural referents unless explicitly stated otherwise or the context clearly indicates otherwise.

Described are compositions and methods of the present invention generally relating to treatment of muscle disorders in a subject in need thereof. According to particular aspects, compositions and methods are provided by the present invention relating to treatment of cardiac muscle disorders in a subject in need thereof.

In specific embodiments, compositions and methods described herein relate to administration of an effective amount of a C-terminal portion of muscle troponin I to a subject in need thereof. In specific embodiments, compositions and methods described herein relate to administration of an effective amount of a C-terminal portion of muscle troponin I which includes the peptide of SEQ ID NO:1 or a variant thereof to a subject in need thereof. In specific embodiments, compositions and methods described herein relate to administration of an effective amount of a nucleic acid encoding a C-terminal portion of muscle troponin I which includes the peptide of SEQ ID NO:1 or a variant thereof to a subject in need thereof.

The term "disorder of cardiac muscle" refers to conditions ameliorated by reduction of muscle sensitivity to Ca$^{2+}$ without decreasing maximum force production. Such conditions include, but are not limited to, heart failure, cardiac disorders relating to mutation of troponin and other sarcomeric proteins, such as hypertrophic cardiomyopathy (HCM), restrictive cardiomyopathy (RCM), and dilated cardiomyopathy (DCM).

According to embodiments, disorders of skeletal muscle are treated by administration of a C-terminal portion of muscle troponin I which includes the peptide of SEQ ID NO:1 or a variant thereof to a subject in need thereof. Disorders of skeletal muscle treated by administration of a C-terminal portion of muscle troponin I which includes the peptide of SEQ ID NO:1 or a variant thereof include coordination disorders of the skeletal muscles.

In specific embodiments, compositions and methods described herein relate to administration of a C-terminal portion of troponin I which includes the peptide of SEQ ID NO:1 or a variant thereof and/or a nucleic acid encoding the peptide or variant thereof to treat diastolic heart failure, i.e., heart failure with preserved ejection fraction, HFpEF.

A subject having a condition ameliorated by reduction of muscle sensitivity to Ca$^{2+}$ without decreasing maximum force production can be identified by a medical professional using standard medical assessment techniques.

In specific embodiments, compositions and methods described herein relate to administration of a peptide including SEQ ID NO:1, or a variant of SEQ ID NO:1, the peptide including SEQ ID NO:1, or variant thereof, having a length of 23 amino acids to 200 amino acids, preferably having a length of 23 amino acids to 35 amino acids. In specific embodiments, compositions and methods described herein relate to administration of a nucleic acid encoding a peptide including SEQ ID NO:1, or a variant of SEQ ID NO:1, the peptide including SEQ ID NO:1, or variant thereof, having a length of 23 amino acids to 200 amino acids, preferably having a length of 23 amino acids to 35 amino acids.

In specific embodiments, compositions and methods described herein relate to administration of a peptide including SEQ ID NO:2, or a variant of SEQ ID NO:2, the peptide or variant having a length of 23 amino acids to 200 amino acids, preferably having a length of 23 amino acids to 35 amino acids. In specific embodiments, compositions and methods described herein relate to administration of a nucleic acid encoding a peptide including SEQ ID NO:2, or a variant of SEQ ID NO:2, and having a length of 23 amino acids to 200 amino acids, preferably having a length of 23 amino acids to 35 amino acids.

In specific embodiments, compositions and methods described herein relate to administration of a peptide including SEQ ID NO:3, or a variant of SEQ ID NO:3, the peptide or variant having a length of 27 amino acids to 200 amino acids, preferably having a length of 27 amino acids to 35 amino acids. In specific embodiments, compositions and methods described herein relate to administration of a nucleic acid encoding a peptide including SEQ ID NO:3, or a variant of SEQ ID NO:3, and having a length of 27 amino acids to 200 amino acids, preferably having a length of 27 amino acids to 35 amino acids.

In specific embodiments, compositions and methods described herein relate to administration of a peptide including SEQ ID NO:4, or a variant of SEQ ID NO:4, the peptide or variant having a length of 27 amino acids to 200 amino acids, preferably having a length of 27 amino acids to 35 amino acids. In specific embodiments, compositions and methods described herein relate to administration of a nucleic acid encoding a peptide including SEQ ID NO:4, or a variant of SEQ ID NO:4, and having a length of 27 amino acids to 200 amino acids, preferably having a length of 27 amino acids to 35 amino acids.

In specific embodiments, compositions and methods described herein relate to administration of a peptide including SEQ ID NO:5, or a variant of SEQ ID NO:5, the peptide or variant having a length of 27 amino acids to 200 amino acids, preferably having a length of 27 amino acids to 35 amino acids. In specific embodiments, compositions and methods described herein relate to administration of a nucleic acid encoding a peptide including SEQ ID NO:5, or a variant of SEQ ID NO:5, and having a length of 27 amino acids to 200 amino acids, preferably having a length of 27 amino acids to 35 amino acids.

In specific embodiments, compositions and methods described herein relate to administration of a peptide including SEQ ID NO:6, or a variant of SEQ ID NO:6, the peptide or variant having a length of 33 amino acids to 200 amino acids, preferably having a length of 33 amino acids to 35 amino acids. In specific embodiments, compositions and methods described herein relate to administration of a nucleic acid encoding a peptide including SEQ ID NO:6, or a variant of SEQ ID NO:6, and having a length of 33 amino acids to 200 amino acids, preferably having a length of 33 amino acids to 35 amino acids.

In specific embodiments, compositions and methods described herein relate to administration of a peptide including SEQ ID NO:7, or a variant of SEQ ID NO:7, the peptide or variant having a length of 27 amino acids to 200 amino acids, preferably having a length of 27 amino acids to 35 amino acids. In specific embodiments, compositions and methods described herein relate to administration of a nucleic acid encoding a peptide including SEQ ID NO:7, or a variant of SEQ ID NO:7, and having a length of 27 amino acids to 200 amino acids, preferably having a length of 27 amino acids to 35 amino acids.

In specific embodiments, compositions and methods described herein relate to administration of a peptide including SEQ ID NO:8, or a variant of SEQ ID NO:8, the peptide or variant having a length of 33 amino acids to 200 amino acids, preferably having a length of 33 amino acids to 35 amino acids. In specific embodiments, compositions and methods described herein relate to administration of a nucleic acid encoding a peptide including SEQ ID NO:8, or a variant of SEQ ID NO:8, and having a length of 33 amino acids to 200 amino acids, preferably having a length of 33 amino acids to 35 amino acids.

In specific embodiments, compositions and methods described herein relate to administration of a peptide including SEQ ID NO:9, or a variant of SEQ ID NO:9, the peptide or variant having a length of 27 amino acids to 200 amino acids, preferably having a length of 27 amino acids to 35 amino acids. In specific embodiments, compositions and methods described herein relate to administration of a nucleic acid encoding a peptide including SEQ ID NO:9, or a variant of SEQ ID NO:9, and having a length of 27 amino acids to 200 amino acids, preferably having a length of 27 amino acids to 35 amino acids.

In specific embodiments, compositions and methods described herein relate to administration of a peptide including SEQ ID NO:10, or a variant of SEQ ID NO:10, the peptide or variant having a length of 27 amino acids to 200 amino acids, preferably having a length of 27 amino acids to 35 amino acids. In specific embodiments, compositions and methods described herein relate to administration of a nucleic acid encoding a peptide including SEQ ID NO:10, or a variant of SEQ ID NO:10, and having a length of 27 amino acids to 200 amino acids, preferably having a length of 27 amino acids to 35 amino acids.

In specific embodiments, compositions and methods described herein relate to administration of a peptide including SEQ ID NO:11, or a variant of SEQ ID NO:11, the peptide or variant having a length of 27 amino acids to 200 amino acids, preferably having a length of 27 amino acids to 35 amino acids. In specific embodiments, compositions and methods described herein relate to administration of a nucleic acid encoding a peptide including SEQ ID NO:11, or a variant of SEQ ID NO:11, and having a length of 27 amino acids to 200 amino acids, preferably having a length of 27 amino acids to 35 amino acids.

In specific embodiments, compositions and methods described herein relate to administration of a peptide including SEQ ID NO:32, or a variant of SEQ ID NO:32, the peptide or variant having a length of 22 amino acids to 200 amino acids, preferably having a length of 22 amino acids to 35 amino acids. In specific embodiments, compositions and methods described herein relate to administration of a nucleic acid encoding a peptide including SEQ ID NO:32, or a variant of SEQ ID NO:32, and having a length of 22 amino acids to 200 amino acids, preferably having a length of 22 amino acids to 35 amino acids.

The term "variant" refers to a peptide functional to reduce cardiac and/or skeletal muscle sensitivity to $Ca^{2+}$ without decreasing maximum force production of the cardiac and/or skeletal muscle and which includes an alteration, i.e. a substitution, insertion or deletion, of one or more amino acids compared to the full-length amino acid sequence of SEQ ID NO:1 while retaining a length in the range of 22 to 200 amino acids, preferably having a length of 22 amino acids to 35 amino acids. The term "variant" refers to both naturally occurring variations of a given peptide and recombinantly prepared mutations of a given peptide, wherein the variant is effective to reduce cardiac and/or skeletal muscle sensitivity to $Ca^{2+}$ without decreasing maximum force production of the cardiac and/or skeletal muscle. Variants of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:32, have at least 80%, or at least 85%, 86%, 87%, 88%, 89%, 90%, 91%, 92%, 93%, 94%, 95%, 96%, 97%, 98%, 99%, or greater, amino acid sequence identity to a full length sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:32, wherein the variant is effective to reduce cardiac and/or skeletal muscle sensitivity to $Ca^{2+}$ without decreasing maximum force production of the cardiac and/or skeletal muscle according to aspects of the present invention.

Particular variants of the peptide of SEQ ID NO:1 are or include SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:32.

```
(core - 23 amino acids)
                                    (SEQ ID NO: 1)
EVGDWRKNIDALSGMEGRKKKFE (core variant - 23 amino acids)
                                    (SEQ ID NO: 2)
(E/D)V(G/T)DWR(K/Q)N(I/V)(D/E)(A/E)(M/L/K)
SGMEGRKK(K/M)F(E/D)

Human cTnI - 27 amino acids.
                                    (SEQ ID NO: 3)
ENREVGDWRKNIDALSGMEGRKKKFES (Salmon cTnI - 27 amino acids)
                                    (SEQ ID NO: 4)
KKEEVTDWRQNVDAMSGMEGRKKMFDA (Toad cTnI - core 27 amino acids)
                                    (SEQ ID NO: 5)
EIREVGDWRKNVDALSGMEGRKKKFES (Toad cTnI - core + C-terminal - 33 amino acids)
                                    (SEQ ID NO: 6)
EIREVGDWRKNVDALSGMEGRKKKFESSGAVQT (Chicken cTnI - core 27 amino acids)
                                    (SEQ ID NO: 7)
ESREVGDWRKNVDALSGMEGRKKKFEA (Chicken cTnI - core + C-termi-
nal - 33 amino acids)
                                    (SEQ ID NO: 8)
ESREVGDWRKNVDALSGMEGRKKKFEAPGGGQG (mouse cTnI and bovine cTnI - 27 amino acids)
                                    (SEQ ID NO: 9)
ENREVGDWRKNIDALSGMEGRKKKFEG Human ssTnI - 34 amino acids.
                                    (SEQ ID NO: 10)
RPVEVGDWRKNVEAMSGMEGRKKMFDAAKSPTSQ Human fsTnI - 29 amino acids.
                                    (SEQ ID NO: 11)
DLRDVGDWRKNIEEKSGMEGRKKMFESES
```

As noted above, a peptide included in compositions and used in methods according to aspects of the present invention has a length in the range of 22 to 200 amino acids, preferably having a length of 22 amino acids to 35 amino acids. In addition to the core minimal peptide of 22 or 23 amino acids or variants thereof detailed in SEQ ID NOs:1, 2, 3, 4, 5, 6, 7, 8, 9, 10, 11, and 32, additional amino acids may be included at the C-terminal, N-terminal, or both the C-terminal and N-terminal of the core peptide of SEQ ID NO:1 or variants according to aspects of the present invention and still retain the functional aspects of the core minimal peptide or variants detailed in SEQ ID NOs:1, 2, 3, 4, 5, 6, 7, 8, 9, 10, 11, and 32, specifically, efficacy to reduce cardiac and/or skeletal muscle sensitivity to $Ca^{2+}$ without decreasing maximum force production of the cardiac and/or skeletal muscle. The additional amino acids can be a particular sequence known to confer a specified function, such as a membrane transport sequence (MTS). Alternatively, the additional amino acids can be portions of a C-terminal portion of troponin I naturally contiguous with the core minimal peptide of 22 or 23 amino acids or variants detailed in SEQ ID NOs:1, 2, 3, 4, 5, 6, 7, 8, 9, 10, 11 and 32.

According to aspects, a peptide for administration to a subject having a cardiac and/or skeletal muscle disorder includes the sequences VGDWRKN (SEQ ID NO:30) and SGMEGRKK (SEQ ID NO:31). These sequences can be linked by a linker, such as a peptide linker or non-peptide linker. Thus, according to aspects, a peptide for administration to a subject having a cardiac and/or skeletal muscle disorder includes the sequence VGDWRKNXXXXSGMEGRKKKFE (SEQ ID NO:32) where each X is any amino acid.

Such additional amino acids can be added to a given amino acid sequence by any of various methods including, but not limited to, recombinant DNA techniques, chemical conjugation and photoconjugation techniques.

Peptides according to aspects of the present invention can be generated by recombinant DNA techniques in vitro, ex vivo, or in vivo, according to aspects of the present invention.

As will be readily apparent to one of skill in the art, due to the redundancy of the genetic code, more than one nucleic acid encodes the peptides according to aspects of the present invention, such as a peptide of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:32.

The term "nucleic acid" as used herein refers to RNA or DNA molecules having more than one nucleotide in any form including single-stranded, double-stranded, oligonucleotide or polynucleotide. The terms "nucleotide sequence" is used to refer to the ordering of nucleotides in an oligonucleotide or polynucleotide in a single-stranded form of nucleic acid.

The term "complementary" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

An example of high stringency hybridization conditions is hybridization of nucleic acids over about 100 nucleotides in length in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL/0.02% polyvinylpyrrolidone.

Mutations can be introduced using standard molecular biology techniques, such as site-directed mutagenesis and PCR-mediated mutagenesis. One of skill in the art will recognize that one or more amino acid mutations can be introduced without altering the functional properties of the peptide of SEQ ID NO:1, a peptide including SEQ ID NO:1, or a variant of either thereof. For example, one or more amino acid substitutions, additions, or deletions can be made without altering the functional properties of the peptide of SEQ ID NO:1, a peptide including SEQ ID NO:1, or a variant of either thereof, SEQ ID NO:2 or a variant thereof, SEQ ID NO:3 or a variant thereof, SEQ ID NO:4 or a variant thereof, SEQ ID NO:5 or a variant thereof, SEQ ID NO:6 or a variant thereof, SEQ ID NO:7 or a variant thereof, SEQ ID NO:8 or a variant thereof, SEQ ID NO:9 or a variant thereof, SEQ ID NO:10 or a variant thereof, or SEQ ID NO:11 or a variant thereof.

Conservative amino acid substitutions can be made in peptides having SEQ ID NO:1, 2, 3, 4, 5, 6, 7, 8, 9, 10, 11, or 32 or including SEQ ID NO:1, 2, 3, 4, 5, 6, 7, 8, 9, 10, 11, or 32 to produce variants according to aspects of the present invention. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, histidine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

Variants according to aspects of the present invention can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

To determine the percent identity of two amino acid sequences or of two nucleotide sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions X100%). In one embodiment, the two sequences are the same length. Alternatively, the two sequences may be different lengths, such as 1, 2, 3, 4, 5, 6, 7, 8, 9 or 10 amino acids different in length. The additions or deletions may be at the N-terminus, C-terminus, internally or a mixture of any thereof.

The determination of percent identity between two sequences can also be accomplished using a mathematical algorithm. A preferred, non-limiting example of a mathematical algorithm utilized for the comparison of two sequences is the algorithm of Karlin and Altschul, 1990, PNAS 87:2264 2268, modified as in Karlin and Altschul, 1993, PNAS. 90:5873 5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the XBLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389 3402. Alternatively, PSI BLAST is used to perform an iterated search which detects distant relationships between molecules. When utilizing BLAST, Gapped BLAST, and PSI Blast programs, the default parameters of the respective programs (e.g., of XBLAST and NBLAST) are used. Another preferred, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

Peptides and variants thereof according to aspects of the present invention can be produced in recombinant host cells using well-known conventional techniques.

Broadly described, an expression cassette includes a nucleic acid encoding a peptide or variant thereof operably linked to one or more regulatory elements that control transcriptional expression of the nucleic acid. An expression cassette can be introduced into a host cell where it is expressed. The expression cassette can be included in an expression vector. The host cell can be in vitro, ex vivo, or in vivo. In the case where the host cell is in vitro or ex vivo, the peptide or variant thereof can be isolated from the host cell and administered to the subject in need thereof.

According to aspects of the present disclosure, the expression cassette includes a nucleic acid encoding a peptide including SEQ ID NO:1, 2, 3, 4, 5, 6, 7, 8, 9, 10, 11, or 32, or a variant of any thereof.

According to aspects of the present disclosure, the expression cassette includes a nucleic acid encoding a peptide including SEQ ID NO:1, 2, 3, 4, 5, 6, 7, 8, 9, 10, 11, or 32, wherein the nucleic acid includes SEQ ID NO:12, 13, 14, 15, 16, 17, 18, 19, 20, 21, or 22.

For in vivo applications, the expression cassette, or expression vector containing the expression cassette, is administered to the subject in need thereof and expression of the peptide occurs in the subject. Thus, according to embodiments of the present invention, expression vector including a nucleic acid encoding a peptide or variant thereof is administered to a subject to treat disorders of skeletal muscle and/or cardiac muscle.

The term "regulatory element" as used herein refers to a nucleotide sequence which controls some aspect of the expression of an operably linked nucleic acid. Exemplary regulatory elements illustratively include an enhancer, an internal ribosome entry site (IRES), an intron; an origin of replication, a polyadenylation signal (pA), a promoter, a transcription termination sequence, and an upstream regulatory domain, which contribute to the replication, transcription, post-transcriptional processing of a nucleic acid. A secretory sequence encoding a secretion signal that directs an encoded heterologous protein into the secretory pathway of a host cell is optionally included. Additional sequences optionally included in an expression vector include one or more sequences encoding a marker suitable for selection of cells carrying the expression vector.

Those of ordinary skill in the art are capable of selecting and using these and other regulatory elements in an expression construct with no more than routine experimentation.

The term "operably linked" as used herein refers to a nucleic acid in functional relationship with a second nucleic acid. The term "operably linked" encompasses functional connection of two or more nucleic acids, such as an oligonucleotide or polynucleotide to be transcribed and a regulatory element such as a promoter or an enhancer element, which allows transcription of the nucleic acid to be transcribed.

The term "promoter" as used herein refers to a DNA sequence operably linked to a nucleic acid to be transcribed such as a nucleic acid encoding a desired molecule. A promoter is generally positioned upstream of a nucleic acid sequence to be transcribed and provides a site for specific binding by RNA polymerase and other transcription factors.

Particular promoters included in operable linkage with a nucleic acid molecule encoding a peptide or variant thereof are functional to preferentially express the operably-linked nucleic acid in a particular cell or tissue type. According to aspects of the present invention, an included promoter is a muscle-specific promoter, such as a skeletal muscle-specific promoter or cardiac muscle-specific promoter. According to aspects of the present invention, an included promoter is selected from: human cardiac troponin I (hcTnI) promoter, human cardiac troponin T (hcTnT) promoter, human cardiac myosin-binding protein C promoter, human cardiac myosin light chain 2V promoter, human alpha cardiac myosin heavy chain promoter, and human beta cardiac myosin heavy chain promoter.

Ubiquitous promoters can be used, such as viral promoters including, but not limited to, CMV, SV40, and others described in detail in M. Y. Rincon, Cardiovascular Research, 108(1):4-20, 2015.

As will be recognized by the skilled artisan, the 5' non-coding region of a gene can be isolated and used in its entirety as a promoter in an expression cassette to drive expression of an operably linked nucleic acid. Alternatively, a portion of the 5' non-coding region can be isolated and inserted in an expression cassette to drive expression of an operably linked nucleic acid. In general, about 500-6000 bp of the 5' non-coding region of a gene is included in an expression cassette to confer expression of the operably linked nucleic acid. Assays which are well-known in the art can be used to determine the ability of a designated portion of the 5' non-coding region of a gene to drive expression of the operably linked nucleic acid.

Promoters described herein are known to be active in mammalian cardiac muscle and/or skeletal muscle. Additional promoters useful in methods and compositions of the present invention may be determined to be active in cardiac muscle and/or skeletal muscle of mammals and other species using conventional techniques, such as analysis of expression of RNA or protein produced from a nucleic acid expression construct in which the promoter is operably linked to a nucleic acid encoding the RNA or protein in cardiac muscle and/or skeletal muscle. Promoter homologues and promoter variants can be included in an expression cassette according to the present invention. The terms "promoter homologue" and "promoter variant" refer to a promoter which has substantially similar functional properties to confer the desired type of expression on an operably linked nucleic acid compared to those disclosed herein.

The term "expression construct" is used herein to refer to a double-stranded recombinant DNA molecule containing a nucleic acid desired to be expressed and containing appropriate regulatory elements necessary or desirable for the transcription of the operably linked nucleic acid sequence in vitro or in vivo. The term "recombinant" is used to indicate a nucleic acid construct in which two or more nucleic acids are linked and which are not found linked in nature. The term "expressed" refers to transcription of a nucleic acid to produce a corresponding mRNA and/or translation of the mRNA to produce the corresponding protein. Expression constructs can be generated recombinantly or synthetically or by DNA synthesis using well-known methodology.

An expression construct is introduced into a cell using well-known methodology, such as, but not limited to, by introduction of a vector containing the expression construct into the cell. A "vector" is a nucleic acid that transfers an inserted nucleic acid into and/or between host cells becoming self-replicating. The term includes vectors that function primarily for insertion of a nucleic acid into a cell, replication of vectors that function primarily for the replication of nucleic acid, and expression vectors that function for transcription and/or translation of a nucleic acid. Also included are vectors that provide more than one of the above functions.

Expression vectors include plasmids, viruses, BACs, YACs, and the like.

Viral expression vectors can be used to express a desired protein or peptide. Non-limiting examples of virus expression systems include adenovirus, adeno-associated virus, herpes virus, vaccinia virus and lentivirus.

A host cell for expression of a peptide or variant thereof can be prokaryotic or eukaryotic, such as bacterial, plant, insect, fungus, yeast, and mammalian cells.

According to aspects of the present invention, the host cell is in vivo, such as in a human, so that the peptide or variant thereof is expressed in the host and treats a disorder of skeletal muscle and/or cardiac muscle in the host.

An expression vector is introduced into a host cell using well-known techniques such as infection or transfection, including calcium phosphate transfection, liposome-mediated transfection, electroporation, sonoporation and nanoparticle-based methodologies. Expression constructs and methods for their generation and use to express a desired protein are known in the art, as described, for example, in Sambrook et al., Molecular Cloning: A Laboratory Manual, Cold Spring Harbor Laboratory Press, 2001; Ausubel, F. et al., (Eds.), Short Protocols in Molecular Biology, Wiley, 2002; and S. J. Higgins and B. D. Hames (Eds.), Protein Expression: A Practical Approach, Oxford University Press, USA, 1999.

In addition to recombinant methodology, chemical synthetic techniques can be used to produce a desired peptide or variant thereof. For example, a peptide or variant thereof can be produced using solid phase synthesis, solution phase synthesis, partial solid phase synthesis or fragment condensation.

A membrane transport sequence (MTS) is optionally covalently or non-covalently attached to a C-terminal portion of cardiac muscle troponin I capable of reduction of muscle sensitivity to $Ca^{2+}$ without decreasing maximum force production and/or a C-terminal portion of skeletal muscle troponin I capable of reduction of muscle sensitivity to $Ca^{2+}$ without decreasing maximum force production of the present invention in order to facilitate transport of the peptide across cell membranes and thereby facilitate intracellular delivery of the peptide.

MTS peptides which facilitate transport across cell membranes are exemplified by, and not limited to, Kaposi fibroblast factor, arginine homopolymer peptide, TAT peptides of HIV-1, Drosophila antennapedia homeodomain-derived peptide, herpes virus protein VP22 and transportan peptide, see G. Guidotti et al., Cell-Penetrating Peptides: From Basic Research to Clinics, 38(4): 406-424, 2017.

An MTS is coupled to a C-terminal portion of cardiac muscle troponin I capable of reduction of muscle sensitivity to $Ca^{2+}$ without decreasing maximum force production and/or a C-terminal portion of skeletal muscle troponin I capable of reduction of muscle sensitivity to $Ca^{2+}$ without decreasing maximum force production of the present invention by any of various methods including, but not limited to, recombinant DNA techniques, chemical conjugation and photoconjugation techniques.

The term "isolated" as used herein refers to a substance that has been separated from contaminating cellular components associated with the substance in nature not intended to be associated with the substance and that would interfere with use of the substance in therapeutic, prophylactic, diagnostic or other uses. Generally, an isolated substance described herein is at least about 80% pure, at least about 90% pure, at least about 95% pure, or greater than about 99% pure. Purification is achieved using well-known standard methodology such as fractionation and/or chromatography, such as ammonium sulfate precipitation and elution chromatography such as size exclusion chromatography, displacement chromatography, ion exchange chromatography and bioaffinity chromatography. Exemplary purification methodology is described in S. Doonan, Protein Purification Protocols Humana Press, 1996.

In embodiments of the present invention, isolated peptide or variant thereof is administered to a subject and/or included in a composition of the present invention.

A C-terminal portion of troponin I included in methods and pharmaceutical compositions according to aspects of the present invention is "isolated" from the remaining portion of troponin I since the remaining portion of troponin I is not present in the pharmaceutical compositions and is not administered to a subject. A C-terminal portion of troponin I as described herein, isolated from the remaining portion of troponin I, is characterized by altered structure and function compared to a C-terminal portion of troponin I disposed in an intact troponin I protein.

An isolated C-terminal portion of troponin I is characterized by altered structural dynamics which results in new functional characteristics, specifically, flexibility and capability to selectively desensitize activated myofilaments with increased relaxation and capability to reduce cardiac muscle and/or skeletal muscle sensitivity to $Ca^{2+}$ without decreasing maximum force production.

According to aspects of the present disclosure, assays for identification of a test compound capable of selectively desensitizing activated myofilaments with increased relaxation are provided. Test compounds identified as having activity to reduce cardiac muscle and/or skeletal muscle sensitivity to $Ca^{2+}$ without decreasing maximum force production may be useful for treating a cardiac muscle disorder and/or skeletal muscle disorder as described herein.

Assays for identification of a test compound capable of selectively desensitizing activated myofilaments with increased relaxation are provided according to aspects of the present disclosure which include contacting human alpha-tropomyosin, or a non-human homologue thereof, with a test compound under conditions that promote specific interaction between the tropomyosin and the test compound, and detecting a change in reducing cardiac muscle and/or skeletal muscle sensitivity to $Ca^{2+}$ without decreasing maximum force production, if present.

The term "test compound" as used herein refers to an agent to be screened for an ability to selectively reduce cardiac muscle and/or skeletal muscle sensitivity to $Ca^{2+}$ without decreasing maximum force production. A test compound can be any of a variety of types of compounds, including chemical compounds, including small organic or inorganic molecules; biological macromolecules such as proteins, peptides, nucleic acids, oligonucleotides, polysaccharides, oligosaccharides; an extract of a biological material, including a cell, a tissue, a plant or plant part, an animal or animal part, bacteria, fungi, or other organisms or biological materials. A test compound which is a small organic or inorganic molecule includes those having a size of less than 500 Daltons, less than 750 Daltons, less than 1000 Daltons, less than 1250 Daltons, less than 1500 Daltons, less than 1750 Daltons, or less than 2000 Daltons.

Collections of test compounds may be used, such as small molecule libraries or combinatorial libraries known in the art, and which may be synthesized using standard methodology or are commercially available. Test compounds in such collections may be assayed individually or as groups of compounds. Optionally, the assay is configured as a high-throughput screening assay in which large numbers of test compounds are assayed in parallel.

Test compounds may be based on modeling the 3-dimensional structure of a C-terminal portion of muscle troponin I and using rational drug design to provide compounds with similar molecular shape, size, charge and hydrophobicity characteristics.

A test compound can be included in an assay in any amount suitable for determining the effect of the compound in an assay for identification of a test compound capable of selectively reducing cardiac muscle and/or skeletal muscle sensitivity to $Ca^{2+}$ without decreasing maximum force production. The appropriate amount of the test compound will depend on various factors such as the particular assay type and the time period over which the effect is assessed, and may be, without limitation, in the range of about 0.001 nM to about 100 mM, about 0.01 nM to about 10 mM, about 0.1 nM to about 1 mM, about 1 nM to about 100 uM, about 10 nM to about 10 uM, or about 100 nM to about 1 uM.

Assay methods according to aspects the present disclosure may be in vivo cell-based assays, or in vitro non-cell-based biochemical or biophysical assays, or in silico.

According to aspects of the present disclosure, assays for identification of test compounds includes assay of the ability of a test compound to selectively reducing cardiac muscle and/or skeletal muscle sensitivity to $Ca^{2+}$ without decreasing maximum force production of muscle cells. Such assays include administering a test compound to ex vivo muscle, e.g. skinned muscle strips and/or skinned muscle sections, connected to a force transducer device and a length controller device, both of which devices can be obtained commercially, and measuring the effect of the test compound on calcium-activated force and/or contractility, for example at pCa 6.5, 6.3, 6.0, 5.8, 5.5, 5.0, and 4.5 at 15° C.

According to aspects of the present disclosure, assays for identification of test compounds includes one or more controls. Controls are well-known in the art and one of skill in the art would readily recognize an appropriate control and be able to determine an appropriate control for an assay method of the present disclosure with no more than routine experimentation. According to aspects of assay methods of the present disclosure, an effect of a test compound is compared to an effect of an isolated C-terminal portion of muscle troponin I, such as an effect of an isolated C-terminal portion of muscle troponin I of SEQ ID NO:1, 2, 3, 4, 5, 6, 7, 8, 9, 10, 11, 32, or a variant of any thereof.

Test substances may be screened for ability to interact with alpha-tropomyosin or a portion containing the binding sites for the isolated C-terminal portion of muscle troponin I, in a cell e.g. in a yeast two-hybrid system.

Figure 12:
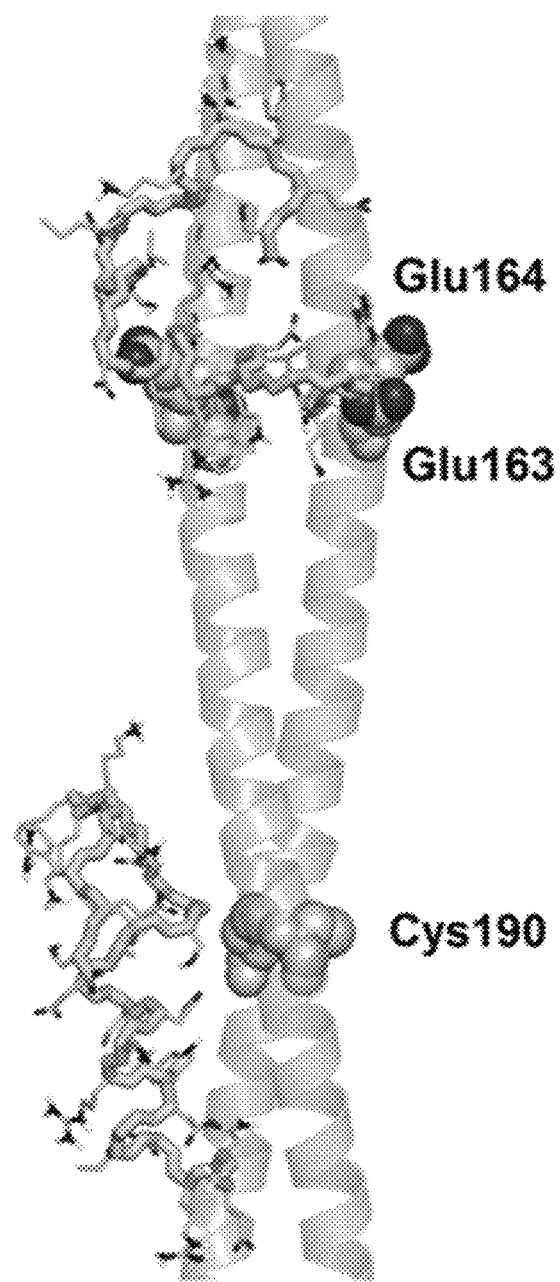
FIG. 12 is a schematic image showing docking of HcTnI-C27 peptide on tropomyosin in molecular dynamic simulation. Representative conformations of HcTnI-C27 peptide in two predicted binding locations of tropomyosin are shown with protein residues of tropomyosin labeled. For clarity, the HcTnI-C27 peptide main chain is represented omitting the O and H atoms. The two docking sites correspond to residues Cys190 and the small acidic patch Glu163-G1u164 in alpha-tropomyosin. The results demonstrate a molecular conformation that favors the stabilization of a helix-like conformation of tropomyosin based on interaction of an isolated C-terminal portion of troponin I, here shown as HcTnI-C27 peptide, forming hydrophobic interactions driven by residues Trp191, Ile195 and Leu198 in HcTnI-C27.

As described and shown herein, a C-terminal portion of muscle troponin I which is isolated from the remainder of muscle troponin I, e.g. by synthesizing the C-terminal portion of muscle troponin I alone, is characterized by altered structural dynamics which results in new functional characteristics, specifically selectively desensitized activated myofilaments with increased relaxation. A specific new functional characteristic of the isolated C-terminal portion of muscle troponin I is the ability to "dock" with tropomyosin thereby reducing cardiac and/or skeletal muscle sensitivity to $Ca^{2+}$ without decreasing maximum force production of the cardiac and/or skeletal muscle. As shown in the image representing molecular dynamic simulation of FIG. 12, the isolated C-terminal portion of muscle troponin I binds at two locations of tropomyosin, the two docking sites correspond to residues Cys190 and the small acidic patch Glu163-Glu164 in human alpha-tropomyosin.

According to aspects of the present disclosure, assays for identification of test compounds which specifically bind to the two docking sites, i.e. binding sites, of alpha-tropomyosin, residue Cys190 and residues Glu163-Glu164, in alpha-tropomyosin are provided according to aspects of the present disclosure which are useful to selectively reduce cardiac muscle and/or skeletal muscle sensitivity to $Ca^{2+}$ without decreasing maximum force production. It is appreciated that analogous binding sites in non-human alpha-tropomyosins will function similarly and that these may be used in an assay according to aspects of the present disclosure.

The ability of a test compound to specifically bind to the two docking sites of alpha-tropomyosin is assessed in vitro according to aspects of the present disclosure.

According to particular aspects of the present disclosure, an in vitro assay includes assay of in vitro motility of regulated actin filaments. Isolated and immobilized myosin motors are used to drive movement of isolated F-actin-tropomyosin-troponin filaments under calcium regulation conditions. The effect of test compounds on a) velocity of the movement, and b) sensitivity of the actin filaments to calcium activation is assessed and may be compared to the effect of an isolated C-terminal portion of muscle troponin I, such as a peptide of SEQ ID NO:1, 2, 3, 4, 5, 6, 7, 8, 9, 10, 11, 32, ora variant of any thereof, on these parameters.

According to particular aspects of the present disclosure, an in vitro assay includes a competition assay wherein a test compound is assayed for the ability to displace an agent with known ability to bind to segments including residue Cys190 and residues Glu163-Glu164 of human alpha-tropomyosin, or analogous residues of a non-human homologue thereof, which binds isolated C-terminal portion of muscle troponin I, such as a peptide of SEQ ID NO:1, 2, 3, 4, 5, 6, 7, 8, 9, 10, 11, 32, or a variant of any thereof. According to particular aspects of the present disclosure, agent with known ability to bind to residue Cys190 and residues Glu163-Glu164 of human alpha-tropomyosin, or analogous residues of a non-human homologue thereof, is an antibody, or binding fragment thereof.

According to particular aspects, an in vitro assay includes a detection of signal modulation, wherein modulation of the signal is indicative of specific interaction of the test compound with the specific binding sites for an isolated C-terminal portion of muscle troponin I in human alpha-tropomyosin, or a non-human homologue thereof. According to particular aspects, human alpha-tropomyosin, or non-human homologue, is detectably labeled at one or both of the specific binding sites for C-terminal portion of muscle troponin I, i.e. residue Cys190 and residues Glu163-Glu164. Specific binding of an isolated C-terminal portion of muscle troponin I to the detectably labeled specific binding site(s) detectably decreases or increases the detected signal emanating from the labeled tropomyosin. Assay of a test compound is performed by contacting the test compound and detectably labeled human alpha-tropomyosin, or non-human homologue, and then assaying for a specific change in detectable signal due to the interaction of the test compound with the labeled tropomyosin. The detectable label can be any label capable of attachment to a protein and which produces a detectable signal modulated by specific binding at or near the site of attachment of the label. According to particular aspects of the present disclosure, the tropomyosin is fluorescently labeled and the fluorescent signal is detected by any of various fluorescence detection apparatus, such as a plate reader, fluorescence microscope, or a fluorometer.

The ability of a test compound to specifically bind to the two docking sites of alpha-tropomyosin is assessed in silico according to aspects of the present disclosure.

A peptide functional to reduce cardiac and/or skeletal muscle sensitivity to $Ca^{2+}$ without decreasing maximum force production of the cardiac and/or skeletal muscle in a subject is administered to a subject in need of treatment of a disorder of skeletal muscle and/or cardiac muscle according to embodiments of the present invention. A peptide functional to reduce cardiac and/or skeletal muscle sensitivity to $Ca^{2+}$ without decreasing maximum force production of the cardiac and/or skeletal muscle in a subject is administered to a subject in need of treatment of a disorder of skeletal muscle and/or cardiac muscle according to embodiments of the present invention, wherein the disorder is cardiac failure. A peptide functional to reduce cardiac and/or skeletal muscle sensitivity to $Ca^{2+}$ without decreasing maximum force production of the cardiac and/or skeletal muscle in a subject is administered to a subject in need of treatment of heart failure, especially diastolic heart failure, i.e., heart failure with preserved ejection fraction, HFpEF, according to embodiments of the present invention, wherein the disorder is cardiac failure.

The terms "treating" and "treatment" used to refer to reduction of cardiac and/or skeletal muscle sensitivity to $Ca^{2+}$ without decreasing maximum force production of the cardiac and/or skeletal muscle in a subject.

A subject treated to reduce cardiac and/or skeletal muscle sensitivity to $Ca^{2+}$ without decreasing maximum force production of the cardiac and/or skeletal muscle according to methods and using compositions of the present invention can be a mammalian subject. Humans are preferred subjects treated according to methods and using compositions of the present invention. A mammalian subject treated according to aspects of the present invention can be any mammal including, but not limited to, a non-human primate; a rodent such as a mouse, rat, or guinea pig; a domesticated pet such as a cat or dog; a horse, cow, pig, sheep, goat, or rabbit. Birds can be treated according to aspects of the present invention, including poultry such as chickens, turkeys, and ducks.

In a particular embodiment of the present invention a method of treating a muscle disorder by reducing cardiac and/or skeletal muscle sensitivity to $Ca^{2+}$ without decreasing maximum force production of the cardiac and/or skeletal muscle in a subject is provided which includes administering a therapeutically effective amount of a peptide or variant thereof to the subject.

A therapeutically effective amount is an amount which produces a desired physiologic or pharmacologic effect in a subject, specifically reducing cardiac and/or skeletal muscle sensitivity to $Ca^{2+}$ without decreasing maximum force production of the cardiac and/or skeletal muscle in a subject having a muscle disorder, such as heart failure.

Suitable dosages ranges of a peptide or variant thereof depend on various factors such as the age of the subject, the extent of muscle disorder in the subject, the general condition of the subject, the route and form of administration of the composition being administered and the particular composition administered. One of ordinary skill in the art will be able to ascertain a therapeutically effective amount without undue experimentation in view of the present disclosure and what is known in the art.

Administration of a peptide or variant thereof according to embodiments of a method of the present invention includes administration according to a dosage regimen to produce a desired response. For example, one or more dosage units of a peptide or variant thereof is administered to a subject at one time in particular embodiments. A suitable schedule for administration of doses depends on several factors including age, weight, medical history and health status of the subject, type of composition used and route of administration, for example. One of skill in the art is able to readily determine a dose and schedule of administration for a particular subject.

According to particular aspects of the present invention, an administered amount of a peptide or variant thereof in the range of about 0.001 mg/kg body weight of the subject to about 100 mg/kg body weight of the subject, such as 0.001 mg/kg, 0.005 mg/kg, 0.01 mg/kg, 0.05 mg/kg, 0.1 mg/kg, 0.5 mg/kg, 1 mg/kg, 5 mg/kg, 10 mg/kg, 50 mg/kg, or 100 mg/kg is administered and will have therapeutic efficacy. The amount may be administered, for example, daily, twice daily, 3 times each day, 4 times each day, 6 times each day or more. The amount may be administered, for example, daily, every other day, every three days, weekly, biweekly or monthly.

A peptide or variant thereof may be administered by any of various routes of administration, for example, oral, rectal, nasal, pulmonary, epidural, ocular, otic, intraarterial, intracardiac, intracerebroventricular, intracranial, intradermal, intravenous, intramuscular, intraperitoneal, intraosseous, intrathecal, intravesical, subcutaneous, topical, transdermal, and transmucosal, such as by sublingual, buccal, vaginal, and inhalational routes of administration. According to particular aspects of the present invention, a peptide or variant thereof is administered intravenously.

Embodiments of the present invention optionally include administration of a therapeutic agent in addition to a peptide or variant thereof. Non-limiting examples of pharmacologically active agents administered in addition to a peptide or variant thereof in combination or separately, according to embodiments of methods of the present invention, include antibiotics, antivirals, antineoplastic agents, analgesics, antipyretics, antidepressants, antipsychotics, anticancer agents, antihistamines, anti-osteoporosis agents, anti-osteonecrosis agents, antiinflammatory agents, anxiolytics, chemotherapeutic agents, diuretics, growth factors, hormones, non-steroidal anti-inflammatory agents and vasoactive agents or a combination of any two or more thereof.

A pharmaceutically acceptable carrier can be included in a composition including a peptide or variant thereof. A pharmaceutically acceptable carrier is substantially non-toxic to the subject in amounts administered and has substantially no deleterious effects on any active component of a composition in which it is included.

The peptide or variant thereof to be administered is formulated for topical, local and/or systemic administration to the subject.

Methods according to embodiments of the present invention include administration of a peptide or variant thereof as pharmaceutical formulations, including those suitable for oral, rectal, nasal, epidural, ocular, otic, intraarterial, intracardiac, intracerebroventricular, intracranial, intradermal, intravenous, intramuscular, intraperitoneal, intraosseous, intrathecal, intravesical, subcutaneous, topical, transdermal, and transmucosal, such as by sublingual, buccal, vaginal, and inhalational routes of administration.

A pharmaceutical formulation of a peptide or variant thereof according to embodiments of the present invention is in any dosage form suitable for administration to a subject, illustratively including solid, semi-solid and liquid dosage forms such as tablets, capsules, powders, granules, suppositories, pills, solutions, suspensions, ointments, lotions, creams, gels, pastes, sprays and aerosols.

Liposomes and emulsions are well-known types of pharmaceutical formulations that can be used to deliver a pharmaceutical agent, particularly a hydrophobic pharmaceutical agent. In embodiments of the present invention, liposomes are particles typically produced as a unilammellar bilayer or a multilammellar bilayer of amphipathic molecules enclosing an aqueous interior. Liposomes can include any type of amphipathic materials compatible with a composition to be delivered, illustratively including naturally-occurring lipids, synthetic lipids and combinations thereof.

A pharmaceutical formulation of a composition of the present invention can include a pharmaceutically acceptable carrier. The term "pharmaceutically acceptable carrier" refers to a carrier which is suitable for use in a subject without undue toxicity or irritation to the subject and which is compatible with other ingredients included in a pharmaceutical composition. Pharmaceutically acceptable carriers, methods for making pharmaceutical compositions and various dosage forms, as well as modes of administration are well-known in the art, for example as detailed in Pharmaceutical Dosage Forms: Tablets, eds. H. A. Lieberman et al., New York: Marcel Dekker, Inc., 1989; and in L. V. Allen, Jr. et al., Ansel's Pharmaceutical Dosage Forms and Drug Delivery Systems, 8th Ed., Philadelphia, PA: Lippincott, Williams & Wilkins, 2004; A. R. Gennaro, Remington: The Science and Practice of Pharmacy, Lippincott Williams & Wilkins, 21st ed., 2005, particularly chapter 89; and J. G. Hardman et al., Goodman & Gilman's The Pharmacological Basis of Therapeutics, McGraw-Hill Professional, 10th ed., 2001.

A solid dosage form for administration or for suspension in a liquid prior to administration illustratively includes capsules, tablets, powders, and granules. In such solid dosage forms, one or more active agents, is admixed with at least one carrier illustratively including a buffer such as, for example, sodium citrate or an alkali metal phosphate illustratively including sodium phosphates, potassium phosphates and calcium phosphates; a filler such as, for example, starch, lactose, sucrose, glucose, mannitol, and silicic acid; a binder such as, for example, carboxymethylcellulose, alginates, gelatin, polyvinylpyrrolidone, sucrose, and acacia; a humectant such as, for example, glycerol; a disintegrating agent such as, for example, agar-agar, calcium carbonate, plant starches such as potato or tapioca starch, alginic acid, certain complex silicates, and sodium carbonate; a solution retarder such as, for example, paraffin; an absorption accelerator such as, for example, a quaternary ammonium compound; a wetting agent such as, for example, acetyl alcohol, glycerol monostearate, and a glycol; an adsorbent such as, for example, kaolin and bentonite; a lubricant such as, for example, talc, calcium stearate, magnesium stearate, a solid polyethylene glycol or sodium lauryl sulfate; a preservative such as an antibacterial agent and an antifungal agent, including for example, sorbic acid, gentamycin and phenol; and a stabilizer such as, for example, sucrose, EDTA, EGTA, and an antioxidant.

Solid dosage forms optionally include a coating such as an enteric coating. The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied having a thickness such that the entire coating does not dissolve in the gastrointestinal fluids at pH below 3 associated with stomach acids, yet dissolves above pH 3 in the small intestine environment. It is expected that any anionic polymer exhibiting a pH-dependent solubility profile is readily used as an enteric coating in the practice of the present invention to achieve delivery of the active agent to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particular enteric coating material includes acrylic acid polymers and copolymers described for example U.S. Pat. No. 6,136,345.

The enteric coating optionally contains a plasticizer to prevent the formation of pores and cracks that allow the penetration of the gastric fluids into the solid dosage form. Suitable plasticizers illustratively include: triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g. hydroxypropylcellulose, acids or bases) to solubilize or disperse the coating material, and to improve coating performance and the coated product.

Liquid dosage forms for oral administration include one or more active agents and a pharmaceutically acceptable carrier formulated as an emulsion, solution, suspension, syrup, or elixir. A liquid dosage form of a composition of the present invention may include a colorant, a stabilizer, a wetting agent, an emulsifying agent, a suspending agent, a sweetener, a flavoring, or a perfuming agent.

For example, a composition for parenteral administration may be formulated as an injectable liquid. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of a desirable particle size in the case of dispersions, and/or by the use of a surfactant, such as sodium lauryl sulfate. A stabilizer is optionally included such as, for example, sucrose, EDTA, EGTA, and an antioxidant.

For topical administration, a composition can be formulated for administration to the skin such as for local effect, and/or as a "patch" formulation for transdermal delivery. Pharmaceutical formulations suitable for topical administration include, for example, ointments, lotions, creams, gels, pastes, sprays and powders. Ointments, lotions, creams, gels and pastes can include, in addition to one or more active agents, a base such as an absorption base, water-removable base, water-soluble base or oleaginous base and excipients such as a thickening agent, a gelling agent, a colorant, a stabilizer, an emulsifying agent, a suspending agent, a sweetener, a flavoring, or a perfuming agent.

Transdermal formulations can include percutaneous absorption enhancers such as acetone, dimethyl acetamide, dimethyl formamide, dimethyl sulfoxide, ethanol, oleic acid, polyethylene glycol, propylene glycol and sodium lauryl sulfate. Ionotophoresis and/or sonophoresis can be used to enhance transdermal delivery.

Powders and sprays for topical administration of one or more active agents can include excipients such as talc, lactose and one or more silicic acids. Sprays can include a pharmaceutical propellant such as a fluorinated hydrocarbon propellant, carbon dioxide, or a suitable gas. Alternatively, a spray can be delivered from a pump-style spray device which does not require a propellant. A spray device delivers a metered dose of a composition contained therein, for example, using a valve for regulation of a delivered amount.

Embodiments of inventive compositions and methods are illustrated in the following examples. These examples are provided for illustrative purposes and are not considered limitations on the scope of inventive compositions and methods.

EXAMPLES

Materials and Methods

Cloning and Bacterial Expression of HcTnI-C27 and R192H Mutant

Figure 2A:
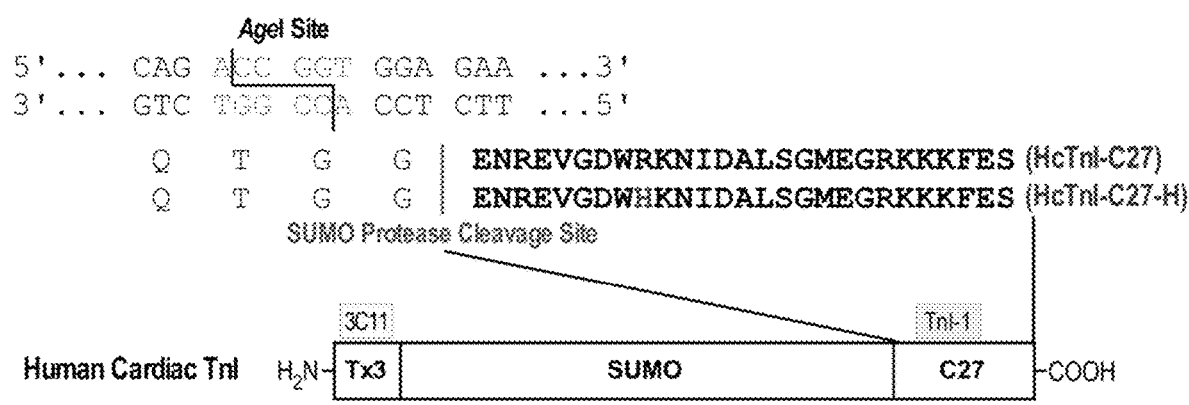
FIG. 2A is a schematic diagram illustrating construction of plasmids expressing HcTnI-C27 and HcTnI-C27-H peptides. HcTnI-C27 and HcTnI-C27-H peptides were expressed as Tx3-SUMO-fusion proteins. The amino acid sequences of HcTnI-C27 and HcTnI-C27-H peptides, the Tx3-SUMO fusion protein structure and the strategy of using AgeI cloning site at the fusion joint for the recovery of free peptide with zero fusion residue are illustrated. The N-terminal Tx3 tag in the fusion protein for metal affinity purification is recognized by an mAb 3C11 for ready identification. Sequences shown in FIG. 2A include CAGACCGGTGGAGAA (SEQ ID NO:24), a cloning vector sequence including an AgeI restriction endonuclease site; and GTCTGGCCACCTCTT (SEQ ID NO:25), a cloning vector sequence complementary to SEQ ID NO:24, and including an AgeI restriction endonuclease site. Also shown is Human cTnI of SEQ ID NO:3 with 4 amino acids at the N-terminus QTGGENREVGDWRKNIDALSGMEGRKKKFES, SEQ ID NO:26, to illustrate the SUMO protease cleavage site; and HcTnT-C27-H of SEQ ID NO:23 with 4 amino acids at the N-terminus QTGGENREVGDWHKNIDALSGMEGRKKKFES, SEQ ID NO:27, to illustrate the SUMO protease cleavage site.

A fusion protein approach was employed to generate biologically synthesized cTnI-C27 peptide. cDNA encoding the C-terminal 27 amino acids of human cardiac TnI (HcTnI-C27) was amplified by polymerase chain reaction (PCR) from a full length cDNA. The forward PCR primer contained a restriction enzyme AgeI site followed by a Gly codon (GGA) required for small ubiquitin-like modifier (SUMO) protease cleavage that leaves zero residue behind, see M. P. Malakhov et al., Journal of Structural and Functional Genomics 5(1-2) (2004) 75-86; A.-M. Catanzariti et al., Protein Science 13(5) (2004) 1331-1339; and C. Amarasinghe et al., Protein and Peptide Letters 22(10) (2015) 885-892 and FIG. 2A. The reverse PCR primer contained a BamHI restriction site previously used to clone the intact cDNA. The PCR product was double-digested with AgeI and BamHI and purified using agarose gel electrophoresis for insertion into a T7 RNA polymerase-based expression plasmid constructed with a transition metal-binding tag (Tx3) and a SUMO substrate domain, see C. Amarasinghe et al., Protein and Peptide Letters 22(10) (2015) 885-892, followed by an in-frame AgeI site and downstream multi-cloning sites. The DNA ligation product was used for transformation of JM109 competent E. coli cells and antibiotic resistant colonies were screened using PCR. Recombinant expression plasmids were miniprepped and sequence confirmed.

Figure 2B:
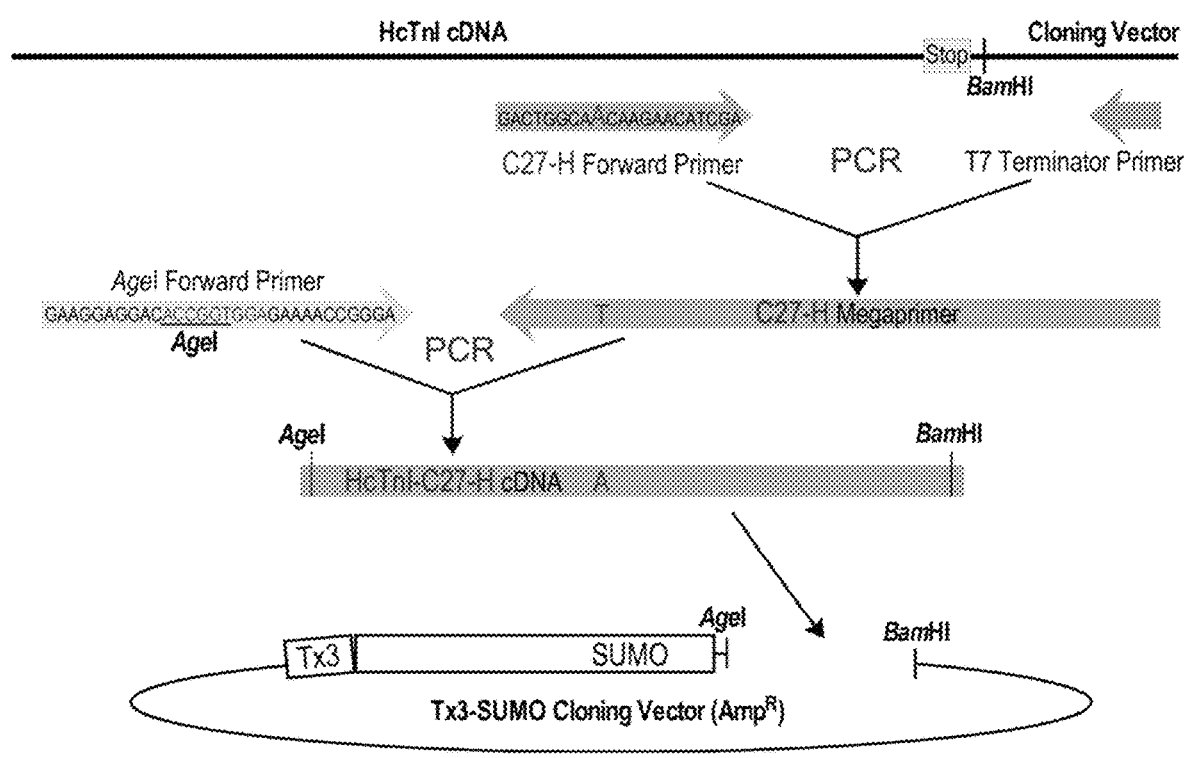
FIG. 2B is a schematic diagram illustrating construction of plasmids expressing HcTnI-C27 and HcTnI-C27-H peptides. The two-step PCR cloning procedure to construct HcTnI-C27-H mutant cDNA into Tx3-SUMO vector is outlined. Sequences shown in FIG. 2B include GACTGGCAACAAGAACATCGA, SEQ ID NO:28, a forward PCR primer specific for a nucleic acid encoding Human cTnI R192H; and GAAGGAGGACACCGGTGGAGAAAACCGGGA, SEQ ID NO:29, a forward PCR primer specific for a nucleic acid encoding Human cTnI R192H to introduce an AgeI restriction endonuclease site into a PCR product as shown.

A recombinant plasmid expressing SUMO-fused HcTnI-C27 containing the RCM mutation R192H (HcTnI-C27-H) was constructed using PCR. A megaprimer was first made by PCR from wild type human cardiac TnI cDNA template using a forward primer containing the mutant site paired with the same reverse primer used above. This PCR-produced megaprimer was purified for use as the reverse primer to pair with the forward primer containing the AgeI restriction site in a second PCR on wild type cDNA template (FIG. 2B). The final PCR product was double-digested using AgeI and BamHI, purified on agarose gel and cloned into Tx3-SUMO plasmid as above.

Sodium Dodecyl Sulfate-Polyacrylamide Gel Electrophoresis (SDS-PAGE)

SDS-PAGE was performed to monitor the expression and identify the C27 peptide in intact TnI and fusion protein constructs. Briefly, 14% Laemmli SDS-PAGE with an acrylamide:bisacrylamide ratio of 29:1 was used to monitor protein expression. Protein samples were prepared by dissolving the proteins in an SDS-PAGE gel sample buffer containing 2% SDS and 3% β-mercaptoethanol. The samples were run on 0.75 mm gels at 20 mA per gel using a Bio-Rad mini-gel system. Resolved gels were stained with Coomassie Blue R-250 and de-stained using 10% acetic acid. The results were documented by imaging using a high resolution scanner.

Tris-Tricine small pore SDS-gels were utilized to resolve small. Briefly, 15% SDS-PAGE with acrylamide:bisacrylamide ratio of 20:1 was used to monitor the recovery of peptides. Samples were prepared as above. The gel was run using different anode and cathode buffers as described in H. Schagger et al., 166(2) (1987) 368-379; J.-P. Jin, Journal of Biological Chemistry 270(12) (1995) 6908-6916. The running conditions and documentation of results were carried out as above.

Western Blotting

The protein bands resolved on SDS-PAGE gels were electrically transferred to nitrocellulose (NC) membranes or polyvinylidene difluoride (PVDF) membranes using a Bio-Rad semidry electrotransfer apparatus at 5 mA per $cm^2$. The membranes were then blocked with 1% bovine serum albumin (BSA) in Tris-buffered saline (TBS) at room temperature for 30 minutes, and incubated with mAb TnI-1 against an epitope in the C-terminal end of TnI or mAb 3C11 against the Tx3 metal affinity purification tag at 4° C. overnight. The TnI-1 mAb was raised using standard hybridoma technology in which the immunization of mouse used purified intact chicken fast TnI. Detailed characterization as reported in J.-P. Jin et al., Biochemistry 40(8) (2001) 2623-2631 demonstrated its specificity against the C-terminal end segment of TnI. The 3C11 mAb was generated using standard hybridoma technology in which the immunization used a Tx3 metal binding tag fusion protein. Detailed characterization as reported in R. Liu, Calponin and Cytoskeleton Dynamics in Macrophage Functions and the Pathogenesis of Atherosclerosis, Wayne State University, Wayne State University Dissertations, 2016, demonstrated its specificity and high affinity against the Tx3 metal binding tag. Washed with 0.05% Triton X-100 and 0.1% SDS in TBS, the membranes were further incubated with alkaline phosphatase-conjugated goat anti-mouse IgG secondary antibody, washed again, and developed in BCIP-NTB substrate solution. The results were documented by imaging using a high resolution scanner.

Expression and Purification of HcTnI-C27 Fusion Protein and Recovery of Free Peptides Sequence-confirmed Tx3-SUMO-HcTnI-C27 and Tx3-SUMO-HcTnI-C27-H expression plasmids were used for transformation of BL21(DE3)pLysS E. coli competent cells. The fusion proteins were expressed in cultures in LB media upon isopropyl β-D-1-thiogalactopyranoside (IPTG) induction at mid-log phase of growth for 3 hours. Bacterial cells were then harvested by centrifugation, resuspended with lysis buffer containing 6 M urea, 1 M KCl, 20 mM phosphate buffer, pH 7.4, supplemented with 5 mM PMSF, and lysed using a French press. Lysate was centrifuged and the supernatant containing the fusion protein was loaded on a Zn(II) affinity column equilibrated with the same buffer. The column was washed with five bed volumes of lysis buffer and the Tx3-fusion protein was eluted with a step gradient of imidazole. The column fractions were examined with SDS-PAGE and the fusion protein peak was pooled, dialyzed against de-ionized water, and concentrated by lyophilization. The lyophilized fusion protein was resuspended in a minimal volume of SUMO cleavage buffer (250 mM NaCl, 250 mM sucrose, 2 mM DTT, 40 mM Tris-HCl, pH 7.5). A 1:200 molar ratio of SUMO protease-to-fusion protein was used to cleave HcTnI-C27 and HcTnI-C27-H peptides at 4° C. overnight. The cleaved product was loaded onto a re-equilibrated Zn(II) affinity column and the flow-through containing free HcTnI-C27 or HcTnI-C27-H peptide was collected, analyzed with small pore SDS-PAGE, dialyzed against de-ionized water, and then concentrated by lyophilization. The fusion proteins and isolated free peptides were used in the following structural and function studies.

Synthetic HcTnI-C27 and HcTnI-C27-H Peptides

Free HcTnI-C27 and HcTnI-C27-H peptides were chemically synthesized at a purity of >98% using a commercial service. After verification of their mAb TnI-1 epitope configuration and tropomyosin binding as described herein, the chemically synthesized peptides were used in skinned muscle contractility studies.

Enzyme-Linked Immunosorbent Assay (ELISA)

The ELISA procedure used in the present study for epitope structure and protein binding studies was performed as described in B. J. Biesiadecki et al., Journal of Biomedicine and Biotechnology, (2011) 1-8. Briefly, 96-well microtiter plates were coated with SUMO-HcTnI-C27 fusion protein, SUMO-HcTnI-C27-H fusion protein, purified bovine cardiac TnI, or R192H mutant mouse cardiac TnI (2 µg/mL in Buffer A containing 0.1 M KCl, 3 mM $MgCl_2$, 10 mM PIPES, pH 7.0, 100 microliters/well) at 4° C. overnight. The plates were washed with Buffer T (0.05% Tween-20 in Buffer A) for 10 minutes and tapped dry. The wells were blocked using Buffer B (1% BSA in Buffer T) at room temperature for one hour. After washing again with Buffer T, serial dilutions of primary mAb against the coated protein were added in triplicates in Buffer D (dilution buffer, 0.1% BSA in Buffer T) and the plate was incubated at room temperature for two hours. After Buffer T washes, horseradish peroxidase (HRP)-conjugated anti-mouse immunoglobulin secondary antibody was added to incubate at room temperature for one hour. After final washes, $H_2O_2$-2,2'-azinobis-(3-ethylbenzthiazolinesulfonic acid) substrate solution was added for colorimetric development at room temperature and the plate was read using an automated microplate reader at 420 nm at 5 minute intervals for 30 minutes.

The ELISA experiments were done in triplicate wells. Optical density data from the time point just before the end of the linear course of color development were used to plot the titration curves. Each experiment was repeated one or more times to confirm the results.

Competitive ELISA

Competitive tropomyosin binding experiments were performed using a derivative protocol of the microtiter plate ELISA as described in B. J. Biesiadecki et al., Journal of Biomedicine and Biotechnology, (2011) 1-8. Purified bovine cardiac α-tropomyosin was coated on 96-well plate at 5 µg/mL in Buffer A at 4° C. overnight. Washed and blocked as above, bovine cardiac TnI was added, at a predetermined concentration that produces sub-maximal binding for the immobilized tropomyosin, to serial dilutions of HcTnI-C27 or HcTnI-C27-H peptides for incubation at room temperature for 2 hours. The competition between the cardiac TnI C-terminal peptides and intact cardiac TnI for tropomyosin binding was measured via mAb 4H6 that recognizes an epitope in intact TnI but not in the C-terminal end peptide, see S. Akhter et al., FEBS Open Bio 5 (2015) 64-75, and HRP-anti-mouse IgG secondary antibody using standard ELISA procedure as described above.

To compare the folding and conformation of chemically synthesized HcTnI-C27 and HcTnI-C27-H peptides with that of the biologically synthesized counterparts, competitive ELISA affinity titrations against mAb TnI-1 were performed. 96-well microtiter plates were coated with purified bovine cardiac TnI in Buffer A and incubated at 4° C. overnight. Monoclonal antibody (mAb) TnI-1 was added, at a predetermined concentration that produces sub-maximal binding for the immobilized bovine cardiac TnI, to serial dilutions of biologically or chemically synthesized HcTnI-C27 and HcTnI-C27-H peptides. The effects of the peptides on competing with intact cardiac TnI for mAb TnI-1 were measured via HRP-anti-mouse IgG secondary antibody using standard ELISA procedure as described above.

Contractility Measurements Using Membrane Permeabilized Muscle Preparations

Extensor digitorum longus (EDL) muscles were obtained from adult C57B/L6 mice immediately after euthanasia to prepare chemically permeabilized muscle preparations as described in J. Ochala et al., The FASEB Journal 25(6) (2011) 1903-1913; and S. M. Roche et al., Journal of Visualized Experiments 100 (2015). Briefly, whole EDL muscles were excised from mice and longitudinally dissected along fibers in a calcium free relaxing buffer. The muscle strips dissected were washed with the relaxing buffer and stored in a 35 mm dish at -20° C. in 50% glycerol relaxing-skinning solution to remove cellular membranes and the endogenous calcium handling system for use in the measurements of calcium sensitivity and force-pCa relationship.

Permeabilized rat and mouse left ventricular papillary muscle preparations were prepared using a skinned cryosection method. Papillary muscles were dissected with a portion of ventricular free wall in one end and valve tendon in the other end. The isolated papillary muscle was pinned down on a cork at the two ends using 30 gauge needles. A small drop of optimal cutting temperature (O.C.T.) compound was used to fill the space between the muscle tissue and the surface of the cork before flash freezing by quickly submerging in liquid nitrogen. The frozen papillary muscle was sectioned longitudinally at a thickness of 35 μm using a cryostat and collected on a glass slide. Four stacked razor blades were used to cut the muscle sections longitudinally into 140-150 μm wide strips. The muscle strips were washed in a relaxing buffer (BES 40 mM, EGTA 10 mM, $MgCl_2$ 6.86 mM, ATP 5.96 mM, DTT 1 mM, creatine phosphate 33 mM, creatine kinase 200 U/mL, K-propionate 3.28 mM, pH 7.0, plus protease inhibitor cocktail) and then gently transferred into myofibril relaxation buffer containing 50% glycerol in a 35 mm culture dish and stored at −20° C. for later use in force-pCa studies.

For contractility studies, the storage dish was placed on a thermal-controlled metal stage at 0° C. under a dissection scope. Cryosectioned cardiac muscle strips selected with cardiomyocytes clearly organized along the long axis and EDL muscle fibers were mounted between two aluminum T-clips and transferred to an 8-chamber thermo-controlled stage (802D, Aurora Scientific) on an inverted microscope in relaxation buffer at 6-8° C. Seen through a 20× lens, the muscle preparation was connected to a force transducer (403A, Aurora Scientific) and a length controller (322-C, Aurora Scientific). The buffer was then switched to a skinning solution (relaxation buffer containing 1% Triton X-100) for 20 min to further permeabilize the muscle strips. After a wash with relaxation buffer, the permeabilized muscle strip was placed in pCa 9.0 buffer made by mixing the relaxing buffer (pCa 10.0) with an activation buffer (BES 40 mM, EGTA 10 mM, $MgCl_2$ 6.64 mM, ATP 6.23 mM, DTT, 1 mM, $CaCl_2$ 10 mM, creatine phosphate 33 mM, creatine kinase 200 U/mL, K-propionate 2.09 mM, pH 7.0, plus protease inhibitor cocktail, pCa 4.0) and the sarcomere length was measured through a digital camera attached to the microscope and adjusted to resting sarcomere length of 2.7 μm for EDL muscle fibers or 2.0 μm and 2.3 μm for cardiac muscle fibers. Calcium activated force was examined at pCa 6.5, 6.3, 6.0, 5.8, 5.5, 5.0, and 4.5 at 15° C. using calcium-EGTA buffer sets made using a formula described in S. M. Roche et al., Journal of Visualized Experiments 100 (2015). HcTnI-C27 peptide was then added at 20 μM and the force-pCa measurements were repeated. The force-pCa curves were plotted and fitted using Hill exponential equation for data analysis, see S. M. Roche et al., Journal of Visualized Experiments 100 (2015).

Data Analysis

Statistical analysis was performed using Student's t-test to compare paired data points.

Results

Biological Synthesis of C-terminal Peptide of Human Cardiac TnI

Figure 3A:
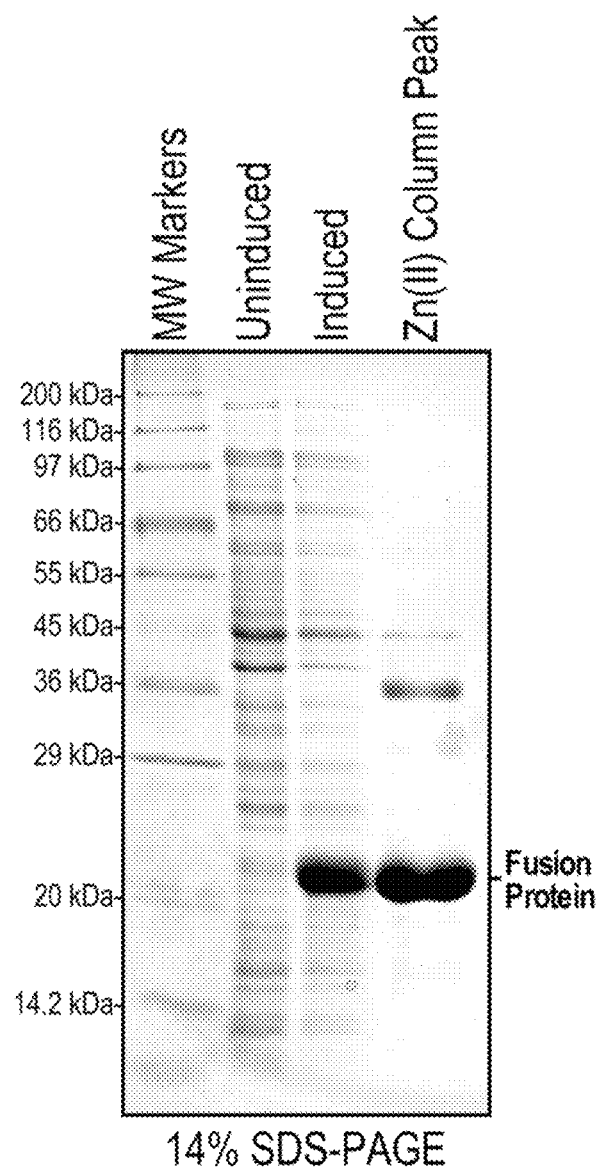
FIG. 3A is an image of an SDS-PAGE showing expression and purification of Tx3-SUMO-HcTnI-C27 and Tx3-SUMO-HcTnI-C27-H fusion proteins and peptide recovery. The SDS-gel shows an example of induced expression of Tx3-SUMO-HcTnI-C27 protein in *E. coli* and effective one-step Zn(II) column purification.

The Tx3-SUMO-HcTnI-C27 fusion protein was readily expressed in *E. coli* and purified using a Zn(II) affinity column, FIG. 3A. Similarly high level expression and effective one-step purification was obtained for the Tx3-SUMO-HcTnI-C27-H fusion protein, FIG. 3B.

Figure 3B:
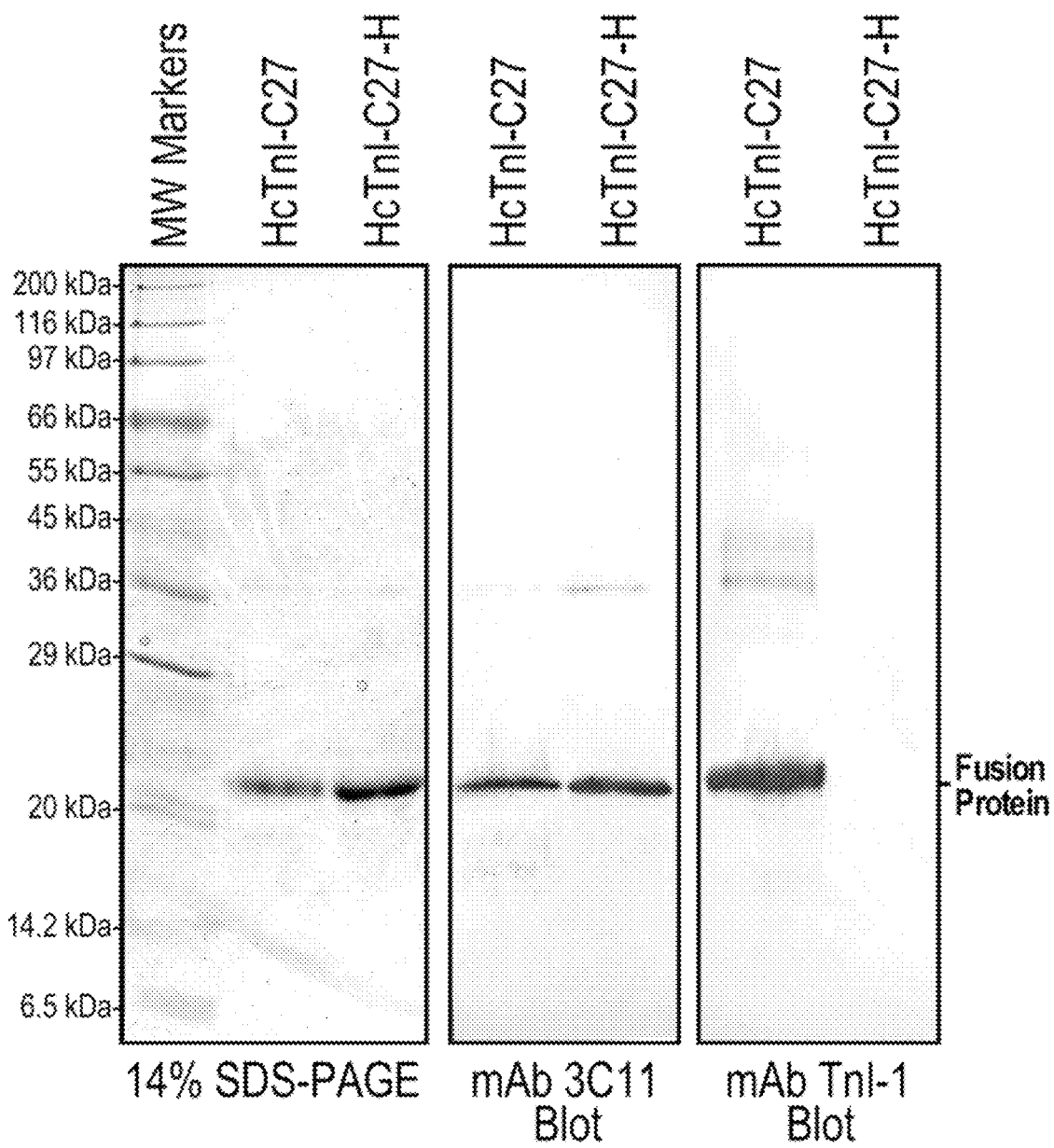
FIG. 3B is an image of an SDS-PAGE and two Western blots showing expression and purification of Tx3-SUMO-HcTnI-C27 and Tx3-SUMO-HcTnI-C27-H fusion proteins and peptide recovery. The Western blots of purified fusion proteins showed that while mAb 3C11 bound to both Tx3-SUMO-HcTnI-C27 and Tx3-SUMO-HcTnI-C27-H via the metal binding tag in the fusion carrier, mAb TnI-1 has a strong binding to Tx3-SUMO-HcTnI-C27 indicating preserved epitope structure, which is abolished in the Tx3-SUMO-HcTnI-C27-H mutant. MW, molecular weight.

While the purified Tx3-SUMO-HcTnI-C27 and Tx3-SUMO-HcTnIC27-H fusion proteins are both recognized by the anti-Tx3 tag mAb3C11 in Western blot, only Tx3-SUMO-HcTnI-C27 was reactive to mAbTnI-1, FIG. 3B. The result is consistent with previous Western blot studies in intact cardiac TnI where the myopathic single amino acid R192H substitution completely abolished the epitope recognized by mAb TnI-1, see Y. Li et al., Journal of Molecular and Cellular Cardiology 62 (2013) 227-236.

The results that the HcTnI-C27 peptide retains the mAb TnI-1 epitope structure when fused with an unrelated carrier protein indicate its retention of a native conformation. This epitope structure is preserved or intrinsically resumed after the denaturing process of SDS-PAGE and Western blotting, FIG. 3B.

Figure 4A:
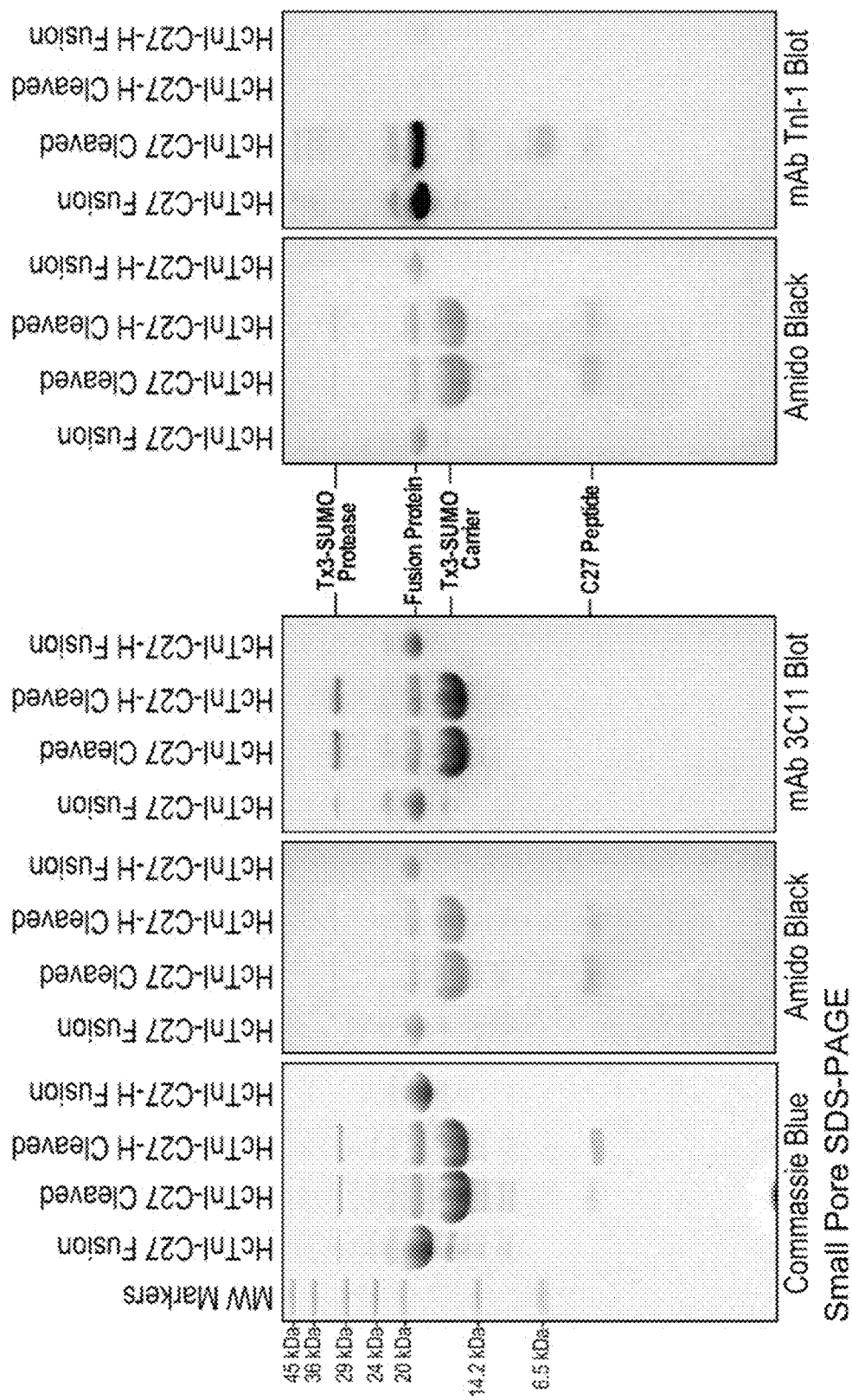
FIG. 4A shows images of a Commassie Blue-stained SDS-PAGE, Amido Black stained membranes after protein transfer from an SDS-PAGE, and Western blots illustrating cleavage of C27 peptides from fusion proteins and preservation of mAb TnI epitope in HcTnI-C27 peptide. The 15% small pore SDS-PAGE gels show the cleavage of Tx3-SUMO-HcTnI-C27 and Tx3-SUMO-HcTnI-C27-H fusion proteins. Western blot using mAb 3C11 against the metal-binding tag in carrier protein detected the intact fusion proteins and the cleaved carrier, as well as the recombinant SUMO protease that also has the metal-binding tag for rapid purification. Western blot using mAb TnI-1 detected the HcTnI-C27 fusion protein and free HcTnI-C27 peptide released by SUMO protease digestion but not the carrier protein. The binding of mAb TnI-1 is lost for the HcTnI-C27-H mutant peptide.

SUMO protease cleavage of the fusion proteins released the HcTnIC27 and HcTnI-C27-H peptides, FIG. 4A. The released peptides were separated from the carrier protein, any un-cleaved fusion protein and the protease, which all have the metal binding tag and were absorbed by the post-cleavage Zn(II) column. The identities of the cleavage products were verified by Western blotting using mAb 3C11 against the Tx3 tag and mAb TnI-1 against the HcTnI-C27 epitope, FIG. 4A. After cleavage from the fusion protein, the isolated HcTnI-C27 peptide remains reactive to mAb TnI-1 in Western blot, FIG. 4A, further demonstrating that this short peptide structure is able to configure the native epitope conformation independently and after the denaturing process of SDS-PAGE and Western blotting, whereas the HcTnI-C27-H mutant peptide cleaved from the fusion protein remains non-reactive to mAb TnI-1, FIG. 4A.

The results demonstrate that the C-terminal end segment of TnI is a structural domain that forms the native conformation when isolated from the TnI backbone. This observation was confirmed by mAb TnI-1 Western blot using chemically synthesized HcTnI-C27 peptide and HcTnI-C27-H mutant peptide, FIG. 4B.

HcTnI-C27 Peptide Retains Native Configuration in Non-Denaturing Conditions

To confirm the initial observation in Western blotting studies, ELISA titrations further showed that Tx3-SUMO-HcTnI-C27 fusion protein reacts with mAb TnI-1 under non-denaturing conditions. The titration curve in FIG. 5A shows a saturable binding of mAb TnI-1 to Tx3-SUMO-HcTnI-C27 fusion protein which is nearly identical to that of the coating control using anti-Tx3 tag mAb 3C11, FIG. 5B.

Figure 4B:
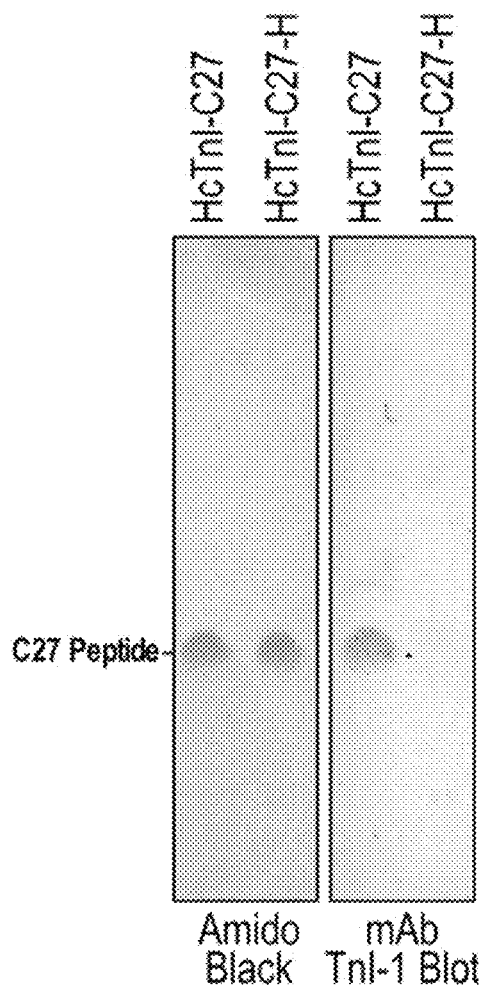
FIG. 4B shows images of an Amido Black stained membrane after protein transfer from an SDS-PAGE and a Western blot illustrating cleavage of C27 peptides from fusion proteins and preservation of mAb TnI epitope in HcTnI-C27 peptide. The preservation of mAb TnI-1 epitope in wild type but not mutant C27 peptide was more clearly demonstrated by Western blot using chemically synthesized peptides. Amido Black stains of the PVDF membranes prior to blocking and mAb incubation are shown to verify the effective blotting of the small peptides. MW, molecular weight.
Figure 5A:
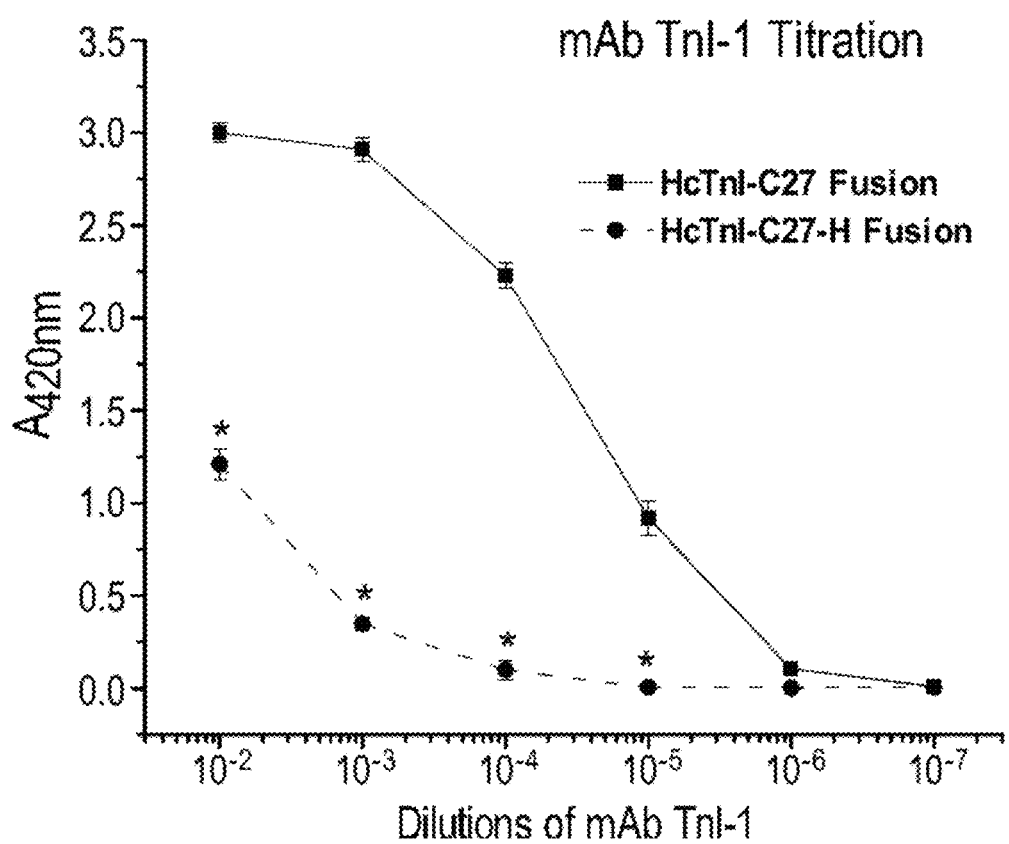
FIG. 5A is a graph showing results of ELISA titration of mAb TnI-1 against Tx3-SUMO-HcTnI-C27 and Tx3-SUMO-HcTnI-C27-H fusion proteins. The fusion proteins were coated on microtiter plate to incubate with serial dilutions of the mAbs for ELISA titration as described in the methods. mAb TnI-1 recognizing the HcTnI-C27 epitope showed high affinity binding to Tx3-SUMO-HcTnI-C27, which was significantly decreased but still clearly detectable for Tx3-SUMO-HcTnI-C27-H. *P<0.0001 in Student's t-test.
Figure 5B:
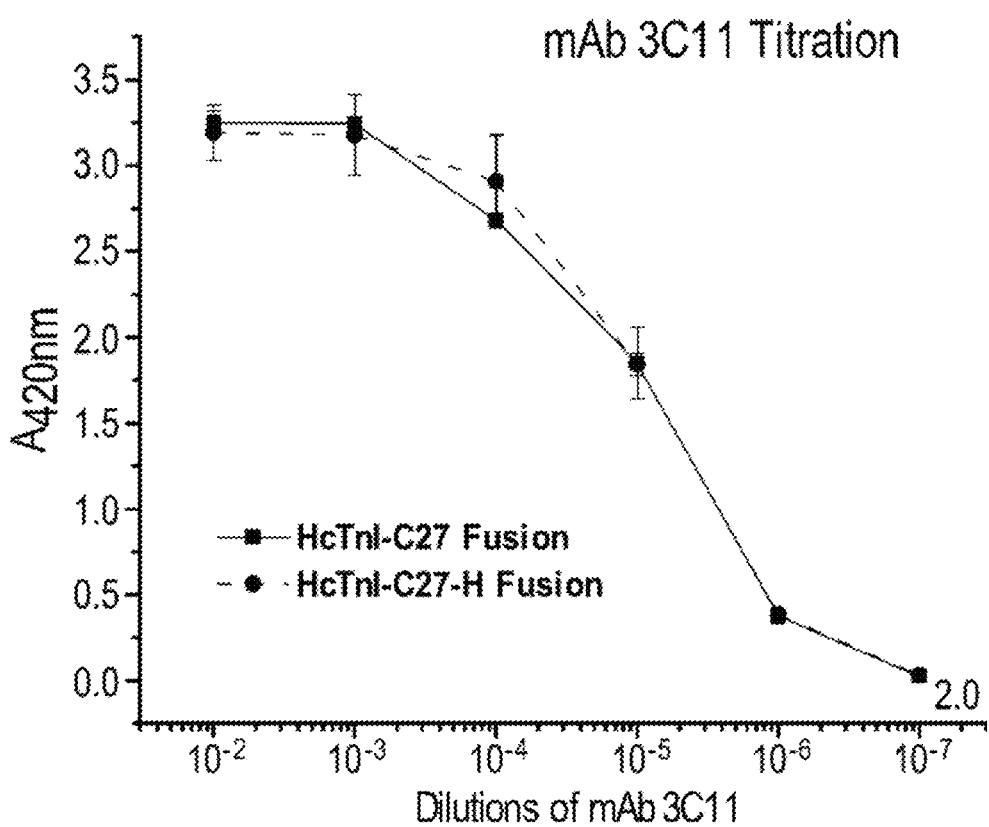
FIG. 5B is a graph showing results of ELISA titration of mAb 3C11 against Tx3-SUMO-HcTnI-C27 and Tx3-SUMO-HcTnI-C27-H fusion proteins. The fusion proteins were coated on microtiter plate to incubate with serial dilutions of the mAbs for ELISA titration as described in the methods. mAb 3C11 titration curves against the metal tag of the fusion proteins confirmed comparable amounts of Tx3-SUMO-HcTnI-C27 and Tx3-SUMO-HcTnI-C27-H coated on the microtiter plate.

While Tx3-SUMO-HcTnI-C27-H lost binding to mAb TnI-1 under the post-denaturing Western blotting condition, FIG. 4B, it showed a clearly detectable but significantly decreased binding to mAb TnI-1 in the ELISA titration using non-denaturing conditions, FIG. 5A. This result demonstrates that while the myopathic R192H mutation alters the conformation and function of the C-terminal end segment of cardiac TnI, the mAb TnI-1 epitope is partially preserved in the Tx3-SUMO-HcTnI-C27-H fusion protein.

Figure 6A:
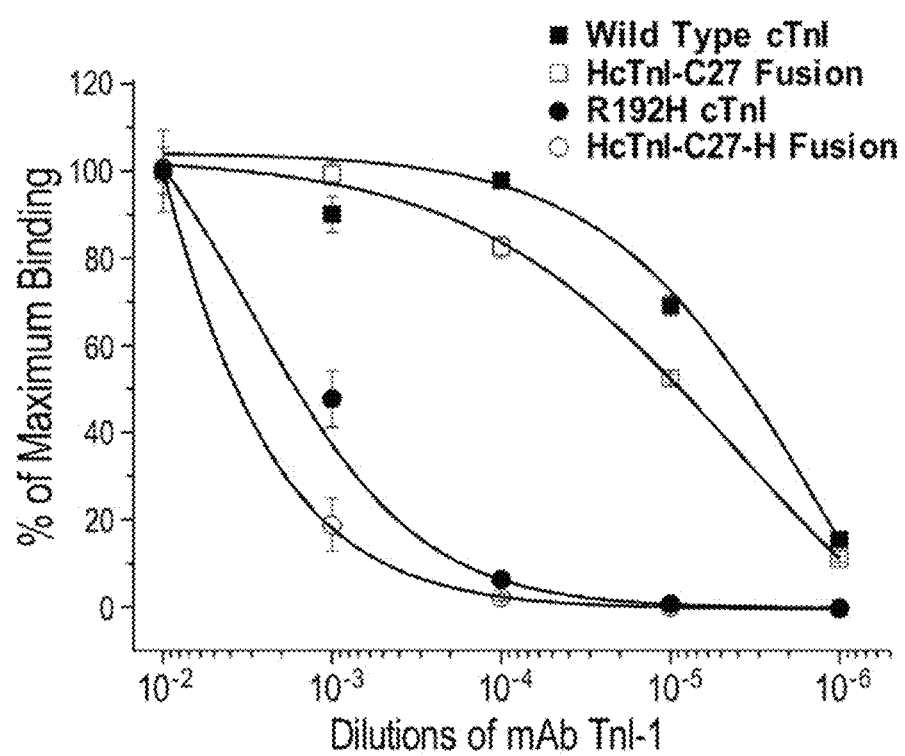
FIGS. 6A and 6B are graphs showing similar affinities of mAb TnI-1 for HcTnI-C27 residing in SUMO fusion protein and in cardiac TnI. The ELISA titration curves normalized to maximum binding in FIG. 6A showed that mAb TnI-1 binds its epitope in Tx3-SUMO-HcTnI-C27 fusion protein and in wild type cardiac TnI (cTnI) with similar affinities as reflected by length of 2.3 µm, however, the addition of HcTnI-C27 peptide significantly decreased Ca$^{2+}$ sensitivity and cooperativity (n), completely diminishing the Ca$^{2+}$-sensitization effect of increasing sarcomere length from 2.0 µm to 2.3 µm. Values are presented as mean±SE. N=4 for SL 2.0 µm group and n=3 for SL 2.3 µm group. The bar graphs show that the maximum force production was not affected by the addition of HcTnI-C27 peptide. Statistical analysis was done using paired Student's t-test. pCa50, Ca$^{2+}$ concentration for 50% maximum force. *P<0.05 vs the SL 2.0 µm control; #P<0.05 vs the SL 2.3 µm baseline in the absence of HcTnI-C27 peptide; § P<0.05 vs SL 2.0 µm control in one-tail Student t-test.
Figure 6B:
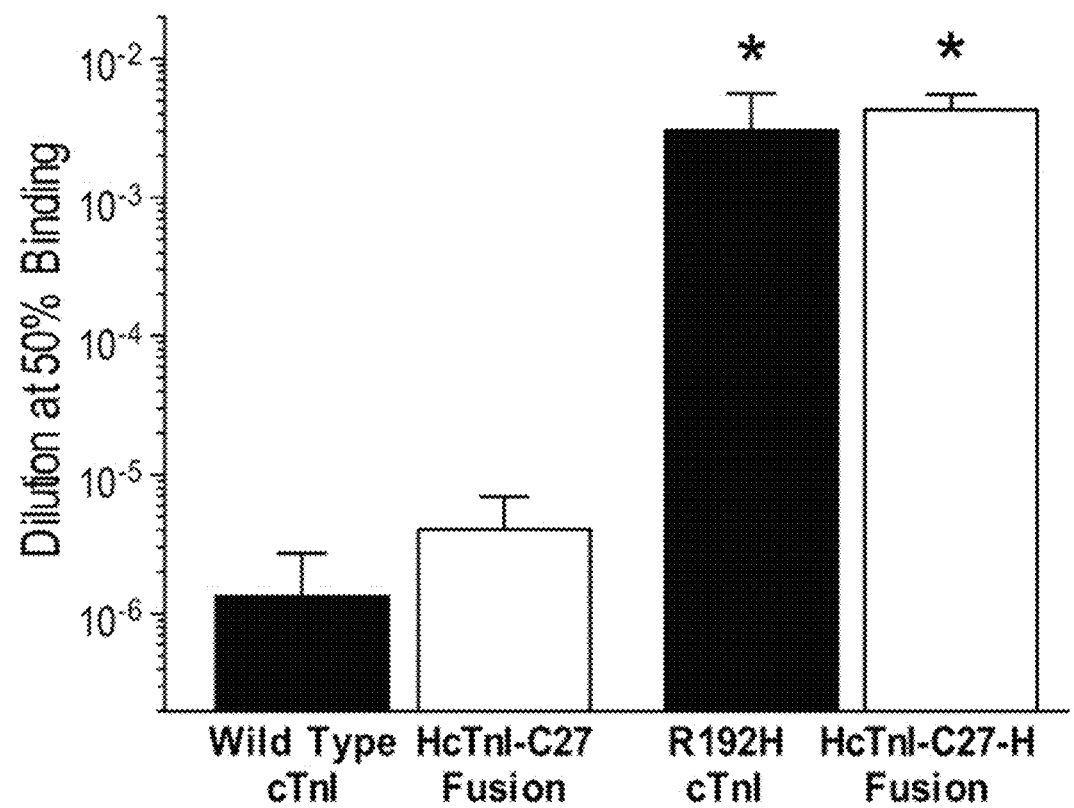

The retained overall native conformation of HcTnI-C27 peptide in the fusion protein and the alteration due to the R192H mutation were further compared to that of the C-terminal end segment residing in situ in intact cardiac TnI. The results of mAb TnI-1 titration in FIG. 6 showed that the binding affinity of Tx3-SUMO-HcTnI-C27 fusion protein for mAb TnI-1 is similar to that of intact wild type bovine cardiac TnI whereas the R192H mutation produced similar decreases in the affinity for mAb TnI-1 in Tx3-SUMO-HcTnI-C27-H fusion protein and in intact mouse cardiac TnI engineered with the RCM mutation. The similar epitope conformation of HcTnI-C27 peptide in fusion with an unrelated carrier protein and in situ in cardiac TnI further demonstrates its nature as an independent structural domain in troponin complex.

HcTnI-C27 Peptide Retains the Property of Binding Tropomyosin

Figure 7:
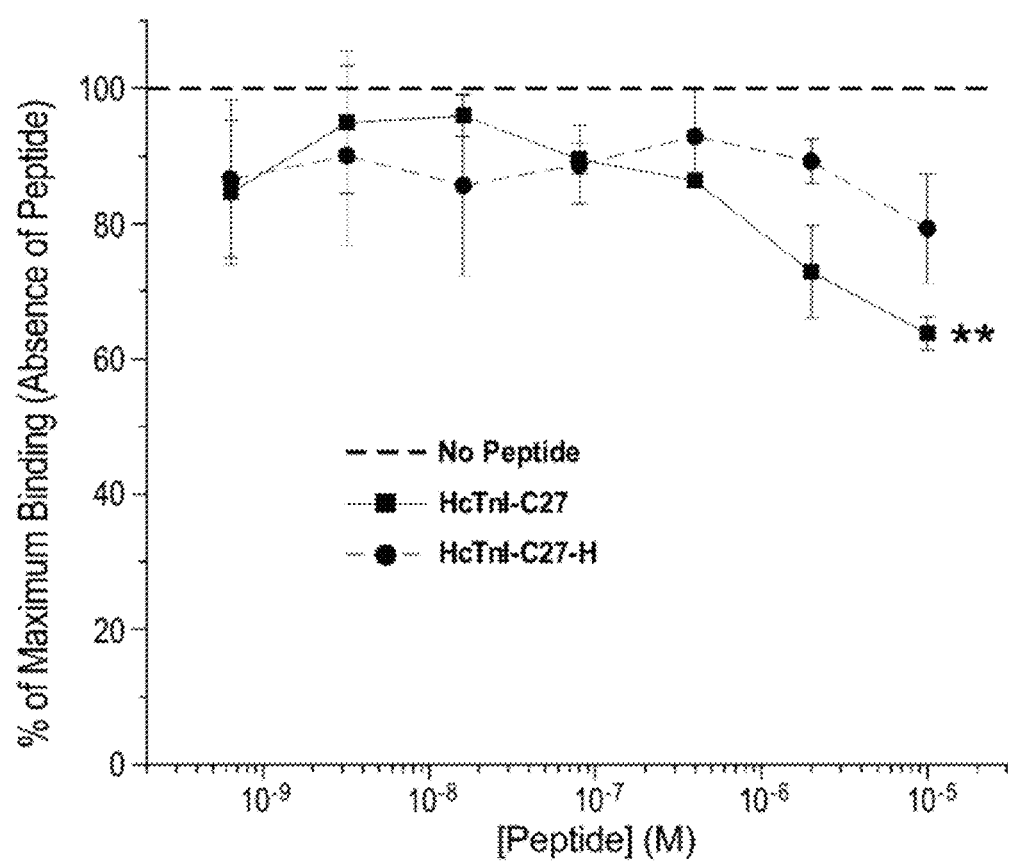
Figure 8A:
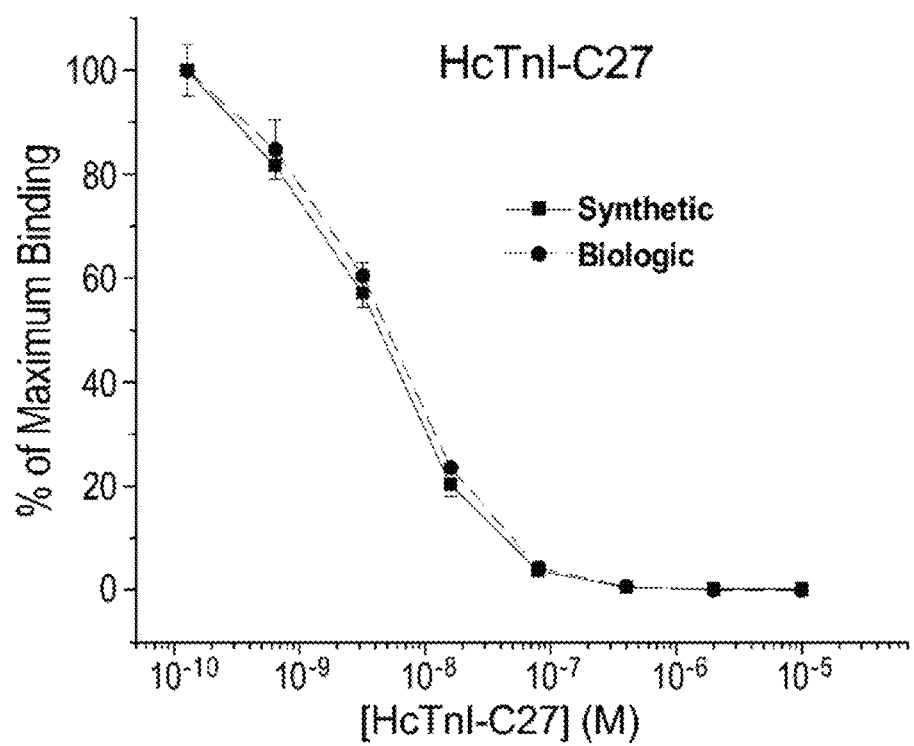
Figure 8B:
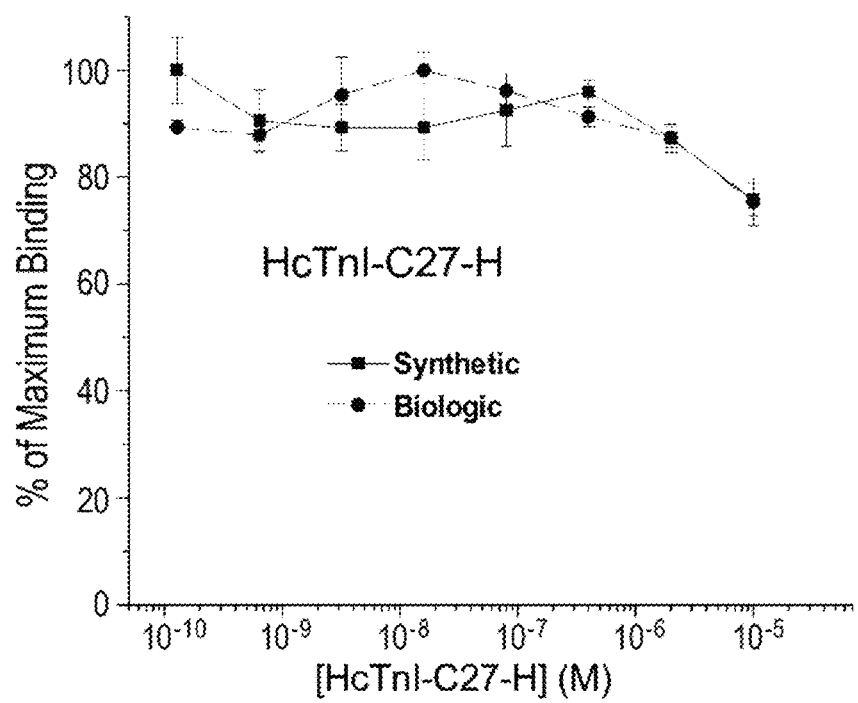
Figure 9:
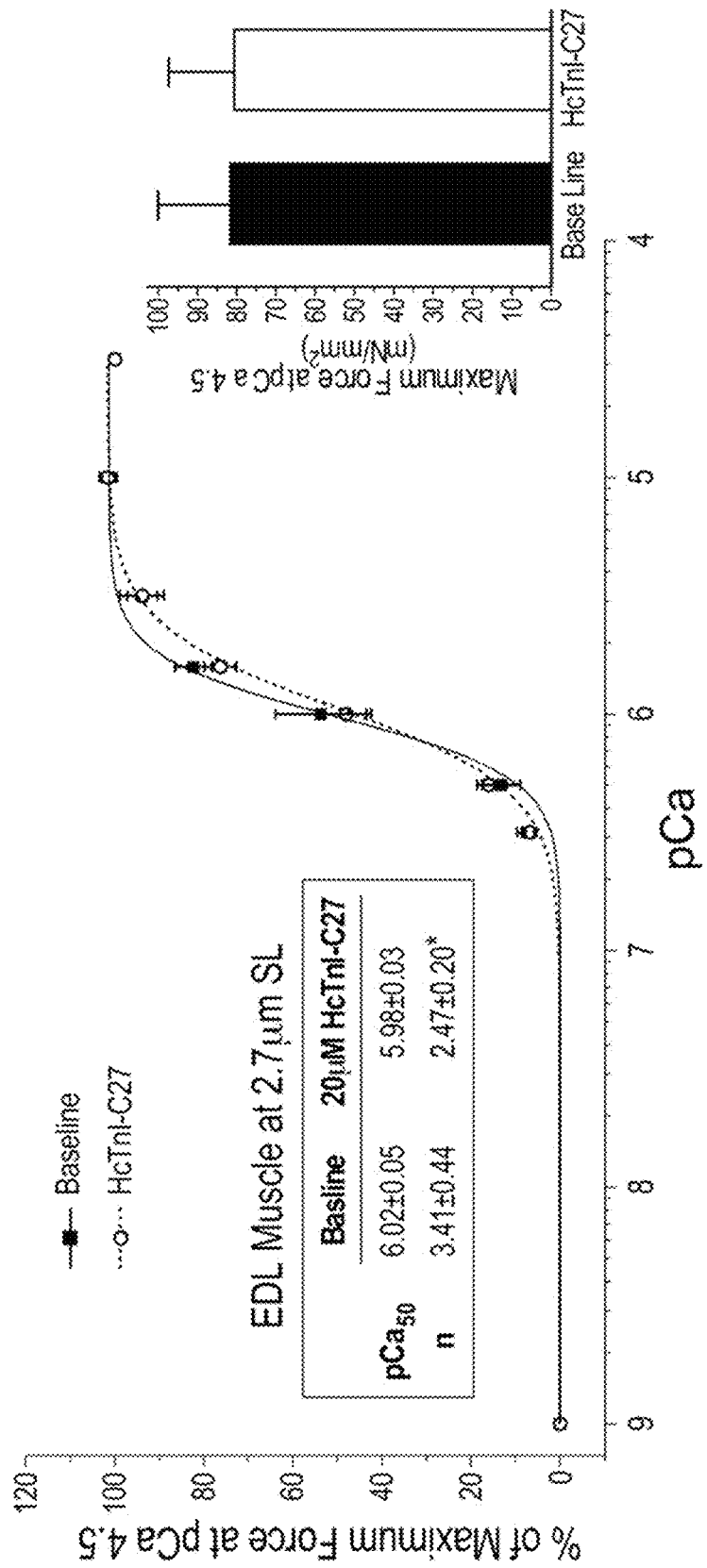
Figure 10A:
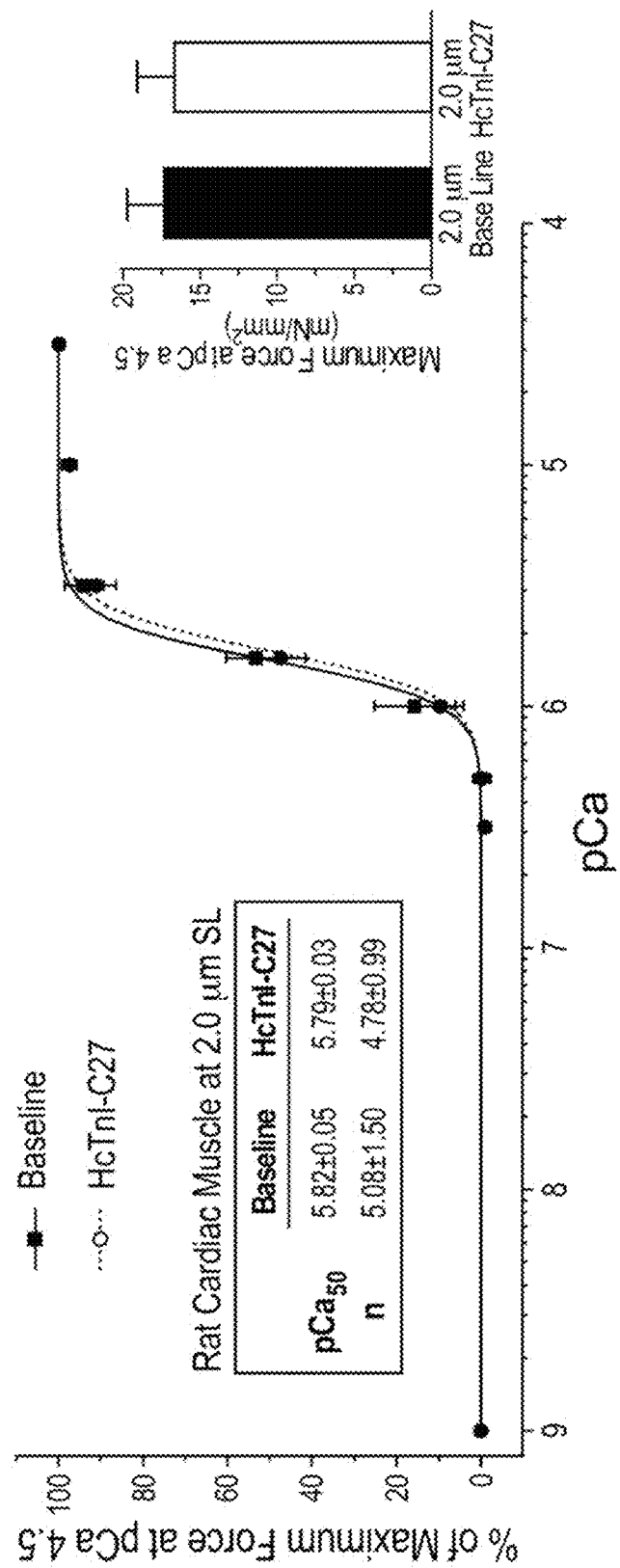
Figure 10B:
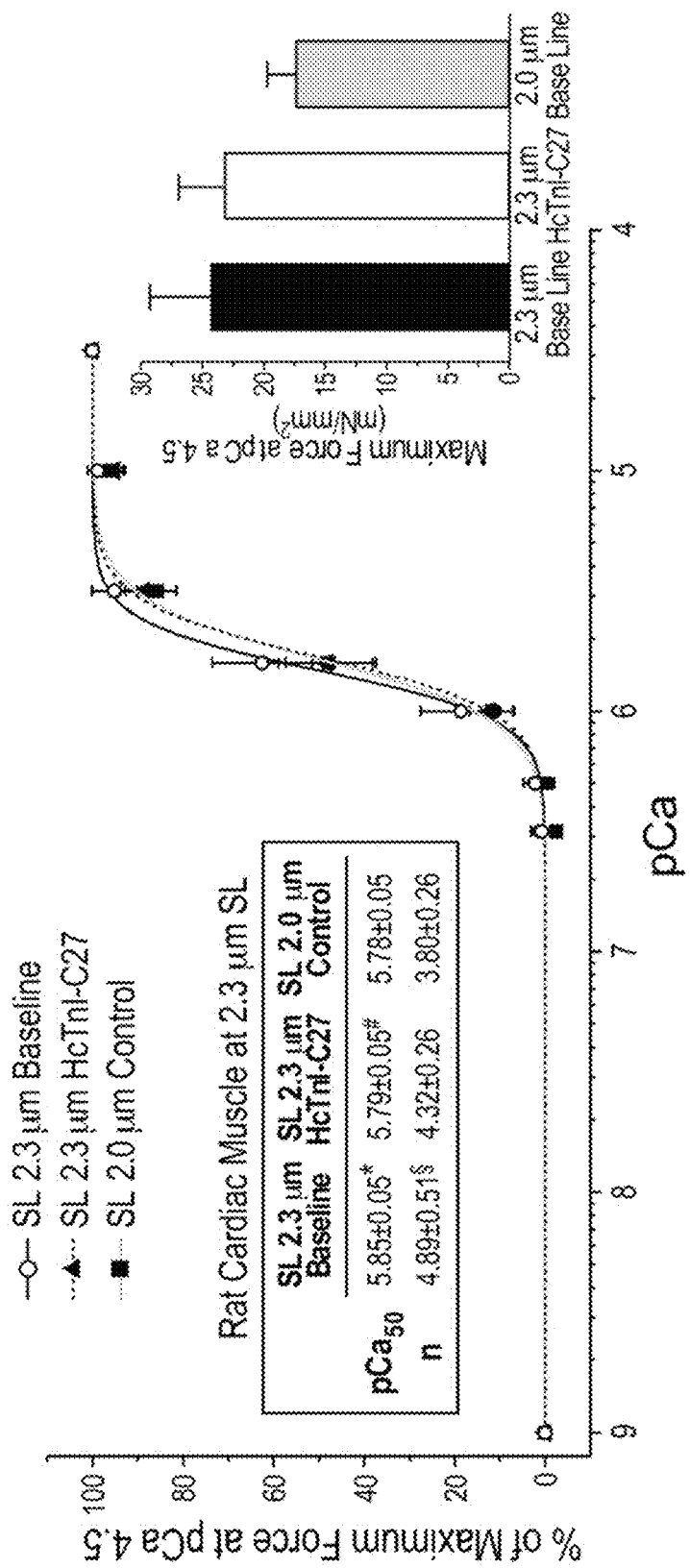
Figure 11A:
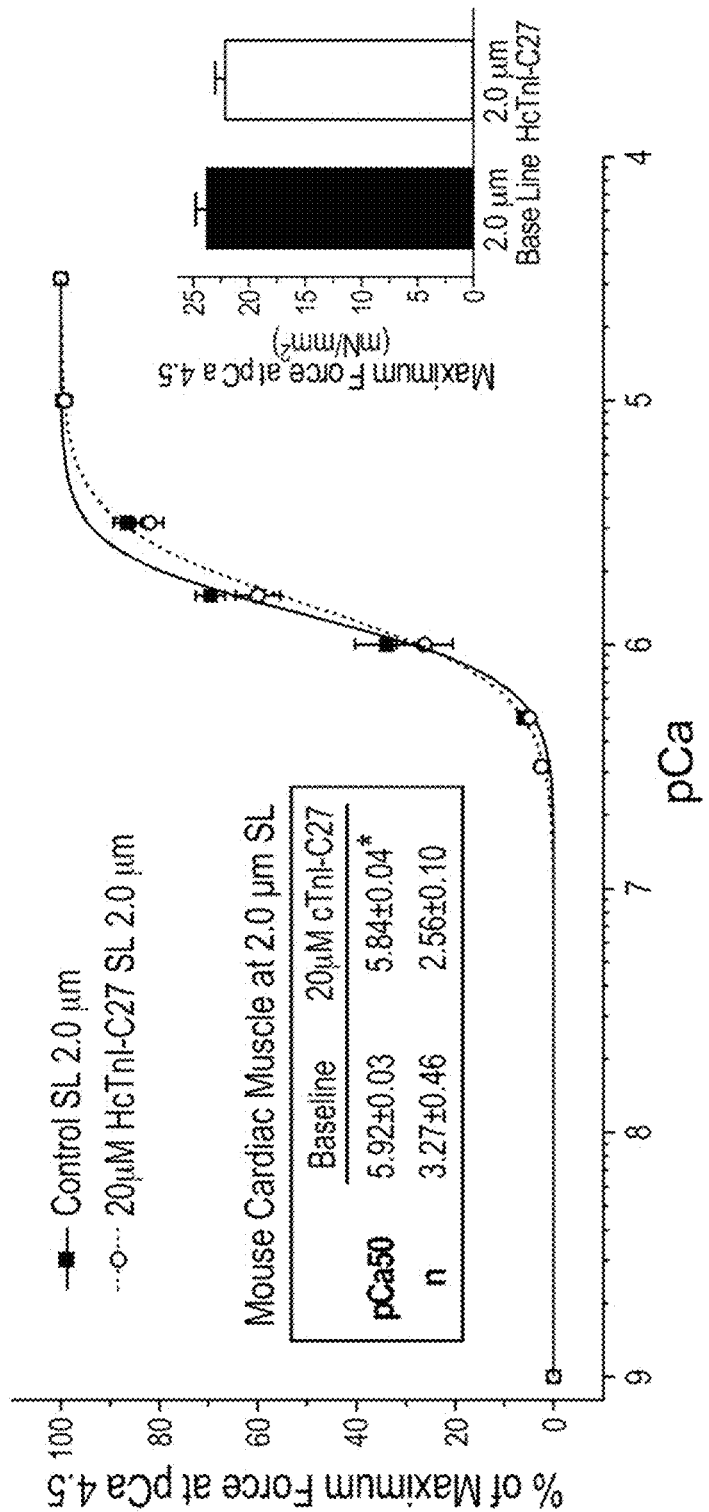
FIGS. 11A and 11B are graphs showing that HcTnI-C27 reduces Ca$^{2+}$ sensitivity of skinned mouse cardiac muscle. The Force-pCa curves show that 20 µM HcTnIC27 treatment decreased Ca$^{2+}$-sensitivity of skinned mouse ventricular papillary muscle at sarcomere lengths (SL) of 2.0 µm, FIG. 11A, and 2.3 µm, FIG. 11B, with decreased cooperativity (n) at SL of 2.0 µm. The maximum force production was not significantly affected by the addition of HcTnIC27 peptide (the bar graphs). pCa50, Ca$^{2+}$ concentration for 50% maximum force. Values are presented as mean±SE. N=3 for 2.0 µm and n=4 for 2.3 µm groups. Statistical analysis was done using paired Student's t-test. *P<0.05 vs the HcTnI-C27 peptide-absent baseline.
Figure 11B:
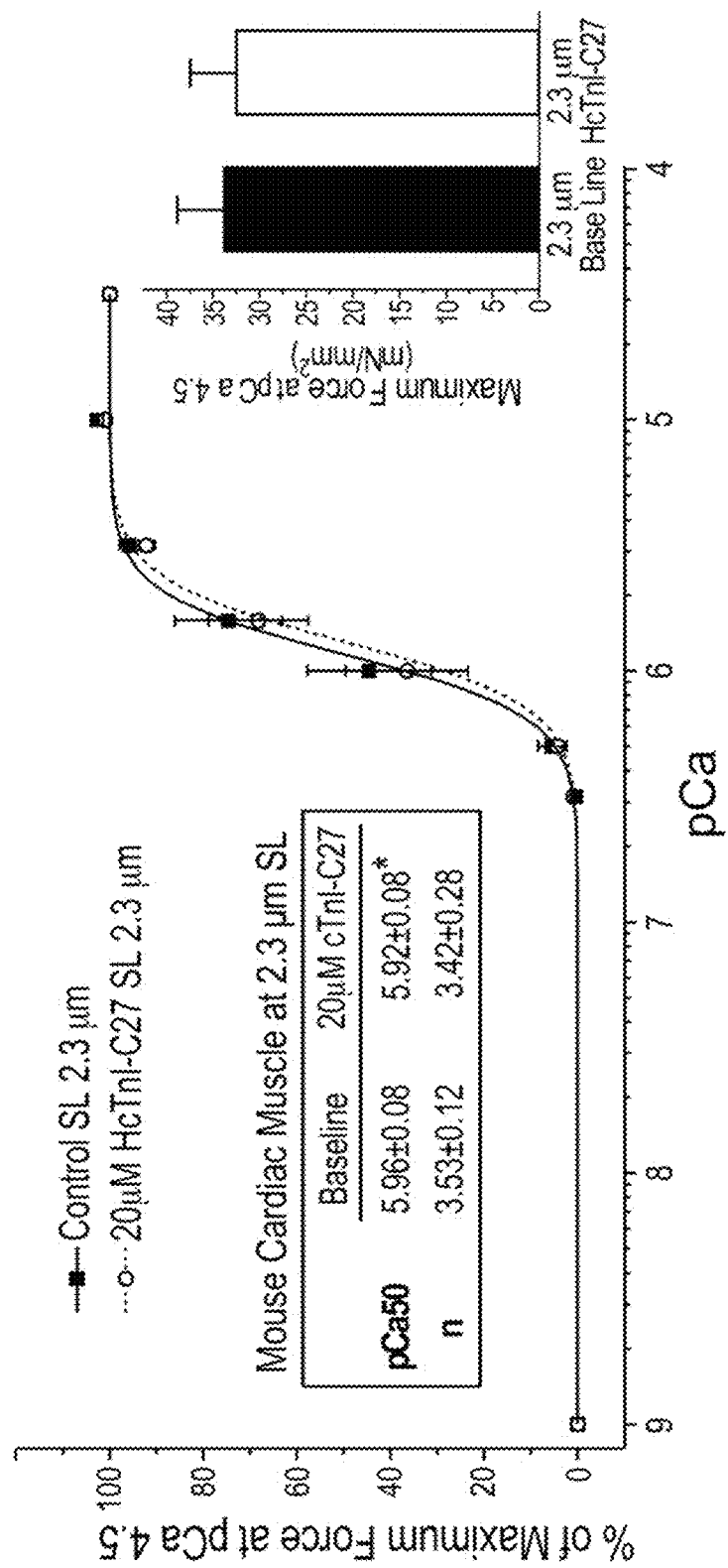

When present in a troponin complex, the C-terminal end segment of TnI possesses a $Ca^{2+}$-regulated, relatively low-affinity but saturable binding to tropomyosin. Demonstrating that this physiologic activity is retained with the isolated HcTnI-C27 peptide, the results of competitive tropomyosin binding test in FIG. 7 showed that the presence of HcTnI-C27 peptide in solution resulted in a dose-dependent competition with intact bovine cardiac TnI for the binding to tropomyosin immobilized on microtiter plate. This function was diminished with the HcTnI-C27-H mutant peptide. The results demonstrate a preserved physiological function of HcTnI-C27 peptide in isolation from the TnI backbone.

Chemically Synthesized HcTnI-C27 and HcTnI-C27-H Peptides Exhibit Epitope Conformations Similar to their Biological-Made Counterparts in Physiologic Solution Upon demonstrating the preserved native conformation and biochemical activity of HcTnI-C27 and HcTnI-C27-H peptides made from bacterial expression, chemically synthesized peptides were evaluated in order to use them in further structural and functional studies. The competitive ELISA titration results in FIG. 8A demonstrated that synthetic and biological-made HcTnI-C27 peptides had nearly identical effectiveness on competing in physiologic solution with intact cardiac TnI coated on microtiter plate for the binding of mAb TnI-1. Consistently, chemically synthesized and biologically made HcTnI-C27-H mutant peptides both drastically lost the binding affinity for mAb TnI-1, FIG. 8B.

HcTnI-C27 Peptide Reduces $Ca^{2+}$ Sensitivity of Skinned Muscle Strips

Since the C-terminal end segment of TnI is conserved in cardiac and skeletal muscle isoforms of TnI, see FIG. 1, HcTnI-C27 peptide was tested for its effect on the contractility of skinned mouse EDL muscle fibers. The results in FIG. 9 showed that at physiologic sarcomere length of 2.7 μm, the presence of 20 μM HcTnI-C27 peptide produced a myofilament $Ca^{2+}$-desensitization effect predominantly in the activated state with significantly decreased cooperativity. The maximum force production was not affected by the addition of HcTnI-C27 peptide. Reproduction of the physiological effect of HcTnI-C27 peptide in a skeletal muscle preparation adds evidence for the conserved function of the C-terminal end segment of TnI.

To investigate the function of the C-terminal end segment of TnI in regulating muscle contraction, the effect of wild type HcTnI-C27 peptide on the force-pCa relationship of cardiac muscle was first studied using skinned rat ventricular papillary muscle sections at sarcomere lengths of 2.0 μm and 2.3 μm. The contractility results in FIG. 10A showed that HcTnI-C27 peptide had a small effect on lowering pCa50 and cooperativity at sarcomere lengths of 2.0 μm. However, it produced a statistically significant right-shift of pCa50 at sarcomere lengths of 2.3 μm with a trend of decreasing cooperativity, FIG. 10B. The maximum force production was not affected by the addition of HcTnIC27 peptide, see the bar graphs in FIGS. 10A and 10B. It is interesting that the effect of HcTnI-C27 on $Ca^{2+}$-desensitization and the effect of increasing sarcomere length on increasing $Ca^{2+}$-sensitivity are both more notable at higher [$Ca^{2+}$ in the isometric contractility assay, corresponding to the activated state of myofilaments, FIG. 10B. As an outcome, the effect of HcTnI-C27 peptide diminished the $Ca^{2+}$-sensitization effect of increasing sarcomere length from 2.0 μm to 2.3 μm, FIG. 10B. The results demonstrate that the addition of free HcTnI-C27 peptide to skinned muscle preparation produces a myofilament activation—as well as sarcomere length-dependent $Ca^{2+}$-desensitization.

The effect of HcTnI-C27 peptide on myofilament $Ca^{2+}$-sensitivity and force development was confirmed using skinned mouse ventricular papillary muscle preparations. The results in FIGS. 11A and 11B showed that the addition of HcTnI-C27 peptide reproduced the $Ca^{2+}$-desensitization effect with right-shifts of the force-pCa curves in skinned mouse cardiac muscle strips. Different from that seen in rat cardiac muscle (FIGS. 10A and 10B), the effect was more obvious at sarcomere length of 2.0 μm in the activated state with significantly lowered cooperativity in comparison to that at sarcomere length of 2.3 μm (FIGS. 11A and 11B). One possible explanation for the different sarcomere length dependence of HcTnI-C27's $Ca^{2+}$ desensitization effect on mouse and rat cardiac muscles could be a species-specific difference in cardiomyocyte compliance, which is known to affect myofilament force-pCa relationships. Supporting this notion, we detected a trend of more increase in the passive tension of skinned mouse cardiac muscle at pCa 9 when increasing the sarcomere length from 2.0 μm to 2.3 μm than that in the rat cardiac muscle preparations. The higher passive tension reflects a lower compliance of mouse cardiac muscle than that of rat, which may confer different myofilament responses to the changes of sarcomere length.

When added to skinned cardiac (FIGS. 9 and 10) and skeletal (FIG. 11) muscle preparations, free HcTnI-C27 peptide produces a $Ca^{2+}$-desensitization effect without significant effect on maximum force production.

The effect of additional free HcTnI-C27 peptide may reflect an artificial augmentation of the in situ inhibitory function of the C-terminal end domain of TnI in facilitating myocardial relaxation. Its effect on decreasing the cooperativity of force-pCa curves reflects a selective decrease of myofilament $Ca^{2+}$-sensitivity at the higher $Ca^{2+}$ concentrations corresponding to the activated state. This new functional feature of the C-terminal end segment of TnI indicates a novel myofilament mechanism to modulate the kinetics of muscle contractility. The post-activation $Ca^{2+}$-desensitization of myofibrils lays a basis for slowing down late-systolic velocity to prolong ventricular ejection time without reducing maximum force development.

Abbreviations cTnI: cardiac troponin subunit I

HcTnI-C27: the C-terminal 27 amino acid peptide of human cardiac TnI

HcTnI-C27-H: R192H mutant of the C-terminal 27 amino acid peptide of human cardiac TnI pCa50: $Ca^{2+}$ concentration for 50% maximum force SUMO: small ubiquitin-like modifier Tx3: a transition metal-binding tag EDL: extensor digitorum longus

```
cDNA sequences:
cDNA sequence encoding SEQ ID NO: 1 (derived from NM_000363.5)
                                                                  (SEQ ID NO: 12)
gaggtgggagactggcgcaagaacatcgatgcactgagtggaatggagggccgcaagaaaaagtttgag cDNA sequence encoding SEQ ID NO: 3 (derived from NM_000363.5)
                                                                  (SEQ ID NO: 13)
gaaaaccgggaggtgggagactggcgcaagaacatcgatgcactgagtggaatggagggccgcaagaaaaagtttgagagc cDNA sequence encoding SEQ ID NO: 4 (derived from NM_001146587.1)
                                                                  (SEQ ID NO: 14)
aagaaagaagaggtcactgactggcgtcaaaatgtggatgccatgtctggcatggagggcagaaagaagatgtttgacgct
```

-continued cDNA sequence encoding SEQ ID NO: 5 (derived from AY773673.1)
(SEQ ID NO: 15)
gaaatacgtgaagttggagactggagaaagaacgtcgatgctctcagcggcatggagggcaggaaaaagaaatttgaatca cDNA sequence encoding SEQ ID NO: 6 (derived from AY773673.1)
(SEQ ID NO: 16)
gaaatacgtgaagttggagactggagaaagaacgtcgatgctctcagcggcatggagggcaggaaaaagaaatttgaatcatctggagca gtgcaaact cDNA sequence encoding SEQ ID NO: 7 (derived from NM_213570.1)
(SEQ ID NO: 17)
gagagccgcgaggtcggcgattggcggaagaacgtggacgcgctgagcggcatggaggggcgcaagaagaagttcgaggcg cDNA sequence encoding SEQ ID NO: 8 (derived from NM_213570.1)
(SEQ ID NO: 18)
gagagccgcgaggtcggcgattggcggaagaacgtggacgcgctgagcggcatggaggggcgcaagaagaagttcgaggcgccgg ggggggggcagggc Mouse cDNA sequence encoding SEQ ID NO: 9 (derived from NM_009406)
(SEQ ID NO: 19)
Gaaaaccgggaggtgggagactggcgcaagaatatcgatgcactgagtggcatggaaggccgcaagaaaaagtttgagggc Bovine cDNA sequence encoding SEQ ID NO: 9 (derived from NM_001040517)
(SEQ ID NO: 20)
Gaaaaccgagaggtgggagactggcgcaagaacattgacgcgttgagtggaatggaaggccgcaagaagaagtttgagggc cDNA sequence encoding SEQ ID NO: 10 (derived from CR541996)
(SEQ ID NO: 21)
cggcctgtggaggtgggtgactggaggaagaacgtggaggccatgtctggcatggaaggccggaagaagatgtttgatgccgccaatgc tccgacctcacaa cDNA sequence encoding SEQ ID NO: 11 (derived from NM_001145829)
(SEQ ID NO: 22)
gacctgcgagacgtgggtgactggaggaagaacatcgaggagaagtctggcatggagggccggaagaagatgtttgagtccgagtcc Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of treating a disorder of cardiac muscle ameliorated by reduction of muscle sensitivity to $Ca^{2+}$ without decreasing maximum force production selected from the group consisting of: heart failure, hypertrophic cardiomyopathy (HCM), restrictive cardiomyopathy (RCM), and dilated cardiomyopathy (DCM) in a subject, comprising:

administering a therapeutically effective dose of an isolated C-terminal portion of troponin I capable of reduction of cardiac muscle and/or skeletal muscle sensitivity to $Ca^{2+}$ without decreasing maximum force production to the subject, wherein the isolated C-terminal portion of troponin I has a length of 23 to 35 amino acids and comprises SEQ ID NO:1.

2. The method of claim 1, wherein the isolated C-terminal portion of troponin I comprises a peptide selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:32.

3. The method of claim 1, wherein the subject is human.

4. The method of claim 1, further comprising administering an additional therapeutic agent.

5. The method of claim 1, wherein administering a therapeutically effective dose of an isolated C-terminal portion of troponin I, comprises administering an expression cassette comprising a nucleic acid encoding the isolated C-terminal portion of troponin I, operably linked to a promoter.

6. The method of claim 5, wherein the promoter is capable of driving expression of the nucleic acid encoding the isolated C-terminal portion of troponin I in cardiac muscle and/or skeletal muscle.

7. The method of claim 5, wherein the promoter is a cardiac muscle protein promoter or a skeletal muscle protein promoter.

8. The method of claim 1, wherein the subject has heart failure.

* * * * *

SEQUENCE LISTING

```
<160> NUMBER OF SEQ ID NOS: 32

<210> SEQ ID NO 1
<211> LENGTH: 23
<212> TYPE: PRT
<213> ORGANISM: Artificial Sequence
<220> FEATURE:
<223> OTHER INFORMATION: C-terminal portion of human cardiac troponin I

<400> SEQUENCE: 1

Glu Val Gly Asp Trp Arg Lys Asn Ile Asp Ala Leu Ser Gly Met Glu
1               5                   10                  15

Gly Arg Lys Lys Lys Phe Glu
            20

<210> SEQ ID NO 2
<211> LENGTH: 23
<212> TYPE: PRT
<213> ORGANISM: Artificial Sequence
<220> FEATURE:
<223> OTHER INFORMATION: Consensus sequence for C-terminal portion of
      cardiac troponin I
<220> FEATURE:
<221> NAME/KEY: MISC_FEATURE
<222> LOCATION: (1)..(1)
```

<223> OTHER INFORMATION: X is Glu or Asp
<220> FEATURE:
<221> NAME/KEY: MISC_FEATURE
<222> LOCATION: (3)..(3)
<223> OTHER INFORMATION: X is Gly or Thr
<220> FEATURE:
<221> NAME/KEY: MISC_FEATURE
<222> LOCATION: (7)..(7)
<223> OTHER INFORMATION: X is Lys or Gln
<220> FEATURE:
<221> NAME/KEY: MISC_FEATURE
<222> LOCATION: (9)..(9)
<223> OTHER INFORMATION: X is Ile or Val
<220> FEATURE:
<221> NAME/KEY: MISC_FEATURE
<222> LOCATION: (10)..(10)
<223> OTHER INFORMATION: X is Asp or Glu
<220> FEATURE:
<221> NAME/KEY: MISC_FEATURE
<222> LOCATION: (11)..(11)
<223> OTHER INFORMATION: X is Ala or Glu
<220> FEATURE:
<221> NAME/KEY: MISC_FEATURE
<222> LOCATION: (12)..(12)
<223> OTHER INFORMATION: X is Met or Leu or Lys
<220> FEATURE:
<221> NAME/KEY: MISC_FEATURE
<222> LOCATION: (21)..(21)
<223> OTHER INFORMATION: X is Lys or Met
<220> FEATURE:
<221> NAME/KEY: MISC_FEATURE
<222> LOCATION: (23)..(23)
<223> OTHER INFORMATION: X is Glu or Asp

<400> SEQUENCE: 2

```
Xaa Val Xaa Asp Trp Arg Xaa Asn Xaa Xaa Xaa Xaa Ser Gly Met Glu
1               5                   10                  15

Gly Arg Lys Lys Xaa Phe Xaa
            20
```

<210> SEQ ID NO 3
<211> LENGTH: 27
<212> TYPE: PRT
<213> ORGANISM: Artificial Sequence
<220> FEATURE:
<223> OTHER INFORMATION: C-terminal portion of human cardiac troponin I

<400> SEQUENCE: 3

```
Glu Asn Arg Glu Val Gly Asp Trp Arg Lys Asn Ile Asp Ala Leu Ser
1               5                   10                  15

Gly Met Glu Gly Arg Lys Lys Lys Phe Glu Ser
            20                  25
```

<210> SEQ ID NO 4
<211> LENGTH: 27
<212> TYPE: PRT
<213> ORGANISM: Artificial Sequence
<220> FEATURE:
<223> OTHER INFORMATION: C-terminal portion of salmon cardiac troponin I

<400> SEQUENCE: 4

```
Lys Lys Glu Glu Val Thr Asp Trp Arg Gln Asn Val Asp Ala Met Ser
1               5                   10                  15

Gly Met Glu Gly Arg Lys Lys Met Phe Asp Ala
            20                  25
```

<210> SEQ ID NO 5
<211> LENGTH: 27
<212> TYPE: PRT
<213> ORGANISM: Artificial Sequence

```
<220> FEATURE:
<223> OTHER INFORMATION: C-terminal portion of toad cardiac troponin I

<400> SEQUENCE: 5

Glu Ile Arg Glu Val Gly Asp Trp Arg Lys Asn Val Asp Ala Leu Ser
1               5                   10                  15

Gly Met Glu Gly Arg Lys Lys Lys Phe Glu Ser
            20                  25

<210> SEQ ID NO 6
<211> LENGTH: 33
<212> TYPE: PRT
<213> ORGANISM: Artificial Sequence
<220> FEATURE:
<223> OTHER INFORMATION: C-terminal portion of toad cardiac troponin I

<400> SEQUENCE: 6

Glu Ile Arg Glu Val Gly Asp Trp Arg Lys Asn Val Asp Ala Leu Ser
1               5                   10                  15

Gly Met Glu Gly Arg Lys Lys Lys Phe Glu Ser Ser Gly Ala Val Gln
            20                  25                  30

Thr

<210> SEQ ID NO 7
<211> LENGTH: 27
<212> TYPE: PRT
<213> ORGANISM: Artificial Sequence
<220> FEATURE:
<223> OTHER INFORMATION: C-terminal portion of chicken cardiac troponin
      I

<400> SEQUENCE: 7

Glu Ser Arg Glu Val Gly Asp Trp Arg Lys Asn Val Asp Ala Leu Ser
1               5                   10                  15

Gly Met Glu Gly Arg Lys Lys Lys Phe Glu Ala
            20                  25

<210> SEQ ID NO 8
<211> LENGTH: 33
<212> TYPE: PRT
<213> ORGANISM: Artificial Sequence
<220> FEATURE:
<223> OTHER INFORMATION: C-terminal portion of chicken cardiac troponin
      I

<400> SEQUENCE: 8

Glu Ser Arg Glu Val Gly Asp Trp Arg Lys Asn Val Asp Ala Leu Ser
1               5                   10                  15

Gly Met Glu Gly Arg Lys Lys Lys Phe Glu Ala Pro Gly Gly Gly Gln
            20                  25                  30

Gly

<210> SEQ ID NO 9
<211> LENGTH: 27
<212> TYPE: PRT
<213> ORGANISM: Artificial Sequence
<220> FEATURE:
<223> OTHER INFORMATION: C-terminal portion of mouse and bovine cardiac
      troponin I

<400> SEQUENCE: 9

Glu Asn Arg Glu Val Gly Asp Trp Arg Lys Asn Ile Asp Ala Leu Ser
1               5                   10                  15
```

Gly Met Glu Gly Arg Lys Lys Phe Glu Gly
            20                  25

<210> SEQ ID NO 10
<211> LENGTH: 34
<212> TYPE: PRT
<213> ORGANISM: Artificial Sequence
<220> FEATURE:
<223> OTHER INFORMATION: C-terminal portion of human slow skeletal
      muscle troponin I

<400> SEQUENCE: 10

Arg Pro Val Glu Val Gly Asp Trp Arg Lys Asn Val Glu Ala Met Ser
1               5                   10                  15

Gly Met Glu Gly Arg Lys Lys Met Phe Asp Ala Ala Lys Ser Pro Thr
            20                  25                  30

Ser Gln

<210> SEQ ID NO 11
<211> LENGTH: 29
<212> TYPE: PRT
<213> ORGANISM: Artificial Sequence
<220> FEATURE:
<223> OTHER INFORMATION: C-terminal portion of human fast skeletal
      muscle troponin I

<400> SEQUENCE: 11

Asp Leu Arg Asp Val Gly Asp Trp Arg Lys Asn Ile Glu Glu Lys Ser
1               5                   10                  15

Gly Met Glu Gly Arg Lys Lys Met Phe Glu Ser Glu Ser
            20                  25

<210> SEQ ID NO 12
<211> LENGTH: 69
<212> TYPE: DNA
<213> ORGANISM: Artificial Sequence
<220> FEATURE:
<223> OTHER INFORMATION: cDNA sequence encoding SEQ ID NO:1

<400> SEQUENCE: 12
gaggtgggag actggcgcaa gaacatcgat gcactgagtg gaatggaggg ccgcaagaaa      60
aagtttgag                                                             69

<210> SEQ ID NO 13
<211> LENGTH: 81
<212> TYPE: DNA
<213> ORGANISM: Artificial Sequence
<220> FEATURE:
<223> OTHER INFORMATION: cDNA sequence encoding SEQ ID NO:3

<400> SEQUENCE: 13
gaaaaccggg aggtgggaga ctggcgcaag aacatcgatg cactgagtgg aatggagggc      60
cgcaagaaaa agtttgagag c                                               81

<210> SEQ ID NO 14
<211> LENGTH: 81
<212> TYPE: DNA
<213> ORGANISM: Artificial Sequence
<220> FEATURE:
<223> OTHER INFORMATION: cDNA sequence encoding SEQ ID NO:4

<400> SEQUENCE: 14
aagaaagaag aggtcactga ctggcgtcaa aatgtggatg ccatgtctgg catggagggc      60

<210> SEQ ID NO 15
<211> LENGTH: 81
<212> TYPE: DNA
<213> ORGANISM: Artificial Sequence
<220> FEATURE:
<223> OTHER INFORMATION: cDNA sequence encoding SEQ ID NO:5

<400> SEQUENCE: 15
gaaatacgtg aagttggaga ctggagaaag aacgtcgatg ctctcagcgg catggagggc    60
aggaaaaaga aatttgaatc a                                              81

<210> SEQ ID NO 16
<211> LENGTH: 99
<212> TYPE: DNA
<213> ORGANISM: Artificial Sequence
<220> FEATURE:
<223> OTHER INFORMATION: cDNA sequence encoding SEQ ID NO:6

<400> SEQUENCE: 16
gaaatacgtg aagttggaga ctggagaaag aacgtcgatg ctctcagcgg catggagggc    60
aggaaaaaga aatttgaatc atctggagca gtgcaaact                           99

<210> SEQ ID NO 17
<211> LENGTH: 81
<212> TYPE: DNA
<213> ORGANISM: Artificial Sequence
<220> FEATURE:
<223> OTHER INFORMATION: cDNA sequence encoding SEQ ID NO:7

<400> SEQUENCE: 17
gagagccgcg aggtcggcga ttggcggaag aacgtggacg cgctgagcgg catggagggg    60
cgcaagaaga agttcgaggc g                                              81

<210> SEQ ID NO 18
<211> LENGTH: 99
<212> TYPE: DNA
<213> ORGANISM: Artificial Sequence
<220> FEATURE:
<223> OTHER INFORMATION: cDNA sequence encoding SEQ ID NO:8

<400> SEQUENCE: 18
gagagccgcg aggtcggcga ttggcggaag aacgtggacg cgctgagcgg catggagggg    60
cgcaagaaga agttcgaggc gccggggggg gggcagggc                           99

<210> SEQ ID NO 19
<211> LENGTH: 81
<212> TYPE: DNA
<213> ORGANISM: Artificial Sequence
<220> FEATURE:
<223> OTHER INFORMATION: cDNA sequence encoding SEQ ID NO:9

<400> SEQUENCE: 19
gaaaaccggg aggtgggaga ctggcgcaag aatatcgatg cactgagtgg catggaaggc    60
cgcaagaaaa agtttgaggg c                                              81

<210> SEQ ID NO 20
<211> LENGTH: 81
<212> TYPE: DNA
<213> ORGANISM: Artificial Sequence
<220> FEATURE:
<223> OTHER INFORMATION: cDNA sequence encoding SEQ ID NO:9

-continued

<400> SEQUENCE: 20
gaaaaccgag aggtgggaga ctggcgcaag aacattgacg cgttgagtgg aatggaaggc    60
cgcaagaaga agtttgaggg c                                              81

<210> SEQ ID NO 21
<211> LENGTH: 102
<212> TYPE: DNA
<213> ORGANISM: Artificial Sequence
<220> FEATURE:
<223> OTHER INFORMATION: cDNA sequence encoding SEQ ID NO:10

<400> SEQUENCE: 21
cggcctgtgg aggtgggtga ctggaggaag aacgtggagg ccatgtctgg catggaaggc    60
cggaagaaga tgtttgatgc cgccaatgct ccgacctcac aa                      102

<210> SEQ ID NO 22
<211> LENGTH: 87
<212> TYPE: DNA
<213> ORGANISM: Artificial Sequence
<220> FEATURE:
<223> OTHER INFORMATION: cDNA sequence encoding SEQ ID NO:11

<400> SEQUENCE: 22
gacctgcgag acgtgggtga ctggaggaag aacatcgagg agaagtctgg catggagggc    60
cggaagaaga tgtttgagtc cgagtcc                                        87

<210> SEQ ID NO 23
<211> LENGTH: 27
<212> TYPE: PRT
<213> ORGANISM: Artificial Sequence
<220> FEATURE:
<223> OTHER INFORMATION: C-terminal portion of human cardiac troponin I
      with H substitution for R at position 9

<400> SEQUENCE: 23

Glu Asn Arg Glu Val Gly Asp Trp His Lys Asn Ile Asp Ala Leu Ser
1               5                   10                  15

Gly Met Glu Gly Arg Lys Lys Lys Phe Glu Ser
            20                  25

<210> SEQ ID NO 24
<211> LENGTH: 15
<212> TYPE: PRT
<213> ORGANISM: Artificial Sequence
<220> FEATURE:
<223> OTHER INFORMATION: cloning vector sequence including an AgeI
      restriction endonuclease site

<400> SEQUENCE: 24

Cys Ala Gly Ala Cys Cys Gly Thr Gly Gly Ala Gly Ala Ala
1               5                   10                  15

<210> SEQ ID NO 25
<211> LENGTH: 15
<212> TYPE: DNA
<213> ORGANISM: Artificial Sequence
<220> FEATURE:
<223> OTHER INFORMATION: cloning vector sequence complementary to SEQ ID
      NO:24 including an AgeI restriction endonuclease site

<400> SEQUENCE: 25
gtctggccac ctctt                                                     15

```
<210> SEQ ID NO 26
<211> LENGTH: 31
<212> TYPE: PRT
<213> ORGANISM: Artificial Sequence
<220> FEATURE:
<223> OTHER INFORMATION: C-terminal portion of human cardiac troponin I
      of SEQ ID NO:3 with four additional amino acids at the N-terminus
      to illustrate the SUMO protease cleavage site

<400> SEQUENCE: 26

Gln Thr Gly Gly Glu Asn Arg Glu Val Gly Asp Trp Arg Lys Asn Ile
1               5                   10                  15

Asp Ala Leu Ser Gly Met Glu Gly Arg Lys Lys Lys Phe Glu Ser
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: C-terminal portion of mutant human cardiac
      troponin I of SEQ ID NO:23 with four additional amino acids at the
      N-terminus to illustrate the SUMO protease cleavage site

<400> SEQUENCE: 27

Gln Thr Gly Gly Glu Asn Arg Glu Val Gly Asp Trp His Lys Asn Ile
1               5                   10                  15

Asp Ala Leu Ser Gly Met Glu Gly Arg Lys Lys Lys Phe Glu Ser
            20                  25                  30

<210> SEQ ID NO 28
<211> LENGTH: 21
<212> TYPE: DNA
<213> ORGANISM: Artificial Sequence
<220> FEATURE:
<223> OTHER INFORMATION: forward PCR primer specific for a nucleic acid
      encoding human cardiac troponin I mutant of SEQ ID NO:23

<400> SEQUENCE: 28
gactggcaac aagaacatcg a                                           21

<210> SEQ ID NO 29
<211> LENGTH: 30
<212> TYPE: DNA
<213> ORGANISM: Artificial Sequence
<220> FEATURE:
<223> OTHER INFORMATION: forward PCR primer specific for a nucleic acid
      encoding human cardiac troponin I mutant of SEQ ID NO:23

<400> SEQUENCE: 29
gaaggaggac accggtggag aaaaccggga                                  30

<210> SEQ ID NO 30
<211> LENGTH: 7
<212> TYPE: PRT
<213> ORGANISM: Artificial Sequence
<220> FEATURE:
<223> OTHER INFORMATION: conserved portion of cardiac troponin I

<400> SEQUENCE: 30

Val Gly Asp Trp Arg Lys Asn
1               5

<210> SEQ ID NO 31
<211> LENGTH: 8
<212> TYPE: PRT
```

-continued

```
<213> ORGANISM: Artificial Sequence
<220> FEATURE:
<223> OTHER INFORMATION: conserved portion of cardiac troponin I

<400> SEQUENCE: 31

Ser Gly Met Glu Gly Arg Lys Lys
1               5

<210> SEQ ID NO 32
<211> LENGTH: 22
<212> TYPE: PRT
<213> ORGANISM: Artificial Sequence
<220> FEATURE:
<223> OTHER INFORMATION: conserved portion of cardiac troponin I with
      variable region
<220> FEATURE:
<221> NAME/KEY: MISC_FEATURE
<222> LOCATION: (8)..(8)
<223> OTHER INFORMATION: X is any amino acid
<220> FEATURE:
<221> NAME/KEY: MISC_FEATURE
<222> LOCATION: (9)..(9)
<223> OTHER INFORMATION: X is any amino acid
<220> FEATURE:
<221> NAME/KEY: MISC_FEATURE
<222> LOCATION: (10)..(10)
<223> OTHER INFORMATION: X is any amino acid
<220> FEATURE:
<221> NAME/KEY: MISC_FEATURE
<222> LOCATION: (11)..(11)
<223> OTHER INFORMATION: X is any amino acid

<400> SEQUENCE: 32

Val Gly Asp Trp Arg Lys Asn Xaa Xaa Xaa Xaa Ser Gly Met Glu Gly
1               5                   10                  15

Arg Lys Lys Lys Phe Glu
            20
```